(12) United States Patent
Katus et al.

(10) Patent No.: US 7,588,756 B1
(45) Date of Patent: Sep. 15, 2009

(54) TREATMENT OF CARDIAC POWER FAILURE

(76) Inventors: Hugo A. Katus, Philosophenweg 17, D-69120 Heidelberg (DE); Andrew Remppis, Vangerowstrasse 2/4, D-69115 Heidelberg (DE); Patrick Most, 1011 Chestnut St., Victoria Bldg., Apt. 702 East, Philadelphia, PA (US) 19107

( * ) Notice: Subject to any disclaimer, the term of this patent is extended or adjusted under 35 U.S.C. 154(b) by 0 days.

(21) Appl. No.: 09/958,053

(22) PCT Filed: Mar. 20, 2000

(86) PCT No.: PCT/EP00/02453

§ 371 (c)(1),
(2), (4) Date: Apr. 30, 2002

(87) PCT Pub. No.: WO00/61742

PCT Pub. Date: Oct. 19, 2000

(30) Foreign Application Priority Data

Apr. 7, 1999 (DE) .................................. 199 15 485

(51) Int. Cl.
*A61K 48/00* (2006.01)
(52) U.S. Cl. .................................... 424/93.2
(58) Field of Classification Search .................. 514/44; 536/23.1; 435/320.1, 455, 456; 424/93.2
See application file for complete search history.

(56) References Cited

U.S. PATENT DOCUMENTS 5,849,528 A * 12/1998 Hillman et al. ............. 435/69.1
6,306,830 B1 * 10/2001 Hammond et al. ............ 514/44

FOREIGN PATENT DOCUMENTS

WO   WO 97/14427   4/1997
WO   WO 98/50079   11/1998

OTHER PUBLICATIONS

Engelkamp et al., Biochemistry 31, 10258-10264, 1992.*
Bonaldo et al., Genome Res. 1996, 6:791-806.*
Adams et al., (Pub-Med[online] Bethesda, MD USA: United States National Library of Medicine [retrieved on Aug. 10, 2004}. Retrieved from: Pub-Med 96026280).*
Anderson et al., Nature, vol. 392, pp. 25-30, Apr. 1998.*
Verma, Nature, vol. 389, pp. 239-242, 1997.*
Orkin et al., "Report and Recommendation of the Panel to Assess the NIH Investment in Research on Gene Therapy" Dec. 7, 1995.*
Bowles et al., Progress in Pediatric Cardiology, 12, 133-145, 2000.*
He et al., "A Simplified System for Generating Recombinant Adenoviruses," *Proc. Natl. Acad. Sci.*, 95:2509-2514 (1998).
Most et al., "S100A1 Adenoviral Gene Transfer Leads to an Increased Velocity of Shortening and Relengthening in Adult Rat Cardiomyocytes," *Circulation*, 100(18):2212, XP-000953109 (1999).
Most et al., "The Hydrophobic Epitopes and the Linker Region of the EF-hand Ca-binding Protein S100A1 Enhance the Caffeine Induced Ca-release from SR," *Circulation*, 100(18):2211 (1999).
Pleger et al., "Increased Heart Function by S100A1 Gene Therapy," *Europ. Heart Journ.*, 20:1984 (1999).
Remppis et al., "Altered Expression of the $Ca^{2+}$-binding Protein S100A1 in Human Cardiomyopathy," *Biochim. Biophys.*, 1313(3):253-257 (1996).
Schäfer and Heizmann, "The S100 Family of EF-hand Calcium-binding Proteins: Functions and Pathology," *TIBS—Trends Biochem. Sci.*, 21(4):134-140 (1996).
Most et al. (1999), XP-002152357, Circulation 110, No. 18, suppl., Nov. 2, 1999, p. I. 420.
Alexander et al., "Gene transfer and models of gene therapy for the myocardium," *Clin. and Exper. Pharmac. and Physiol.* 26:661-668 (1999).
Barr et al., "Efficient catheter-mediated gene transfer into the heart using replication-defective adenovirus," *Gene Ther.* 1:51-58 (1994).
Donahue et al., "Ultrarapid, highly efficient viral gene transfer to the heart," *Proc. Natl. Acad. Sci. USA* 94:4664-4668 (1997).
Maurice et al., "Enhancement of cardiac function after adenoviral-mediated in vivo intracoronary $\beta_2$-adrenergic receptor gene delivery," *J. Clin Invest.* 104(1):21-29 (1999).
Pleger et al., "S100A1 Gene therapy preserves in vivo cardiac function after myocardial infarction," *Mol. Ther.* 12(6):1120-1129 (2005).

* cited by examiner

*Primary Examiner*—Brian Whiteman
(74) *Attorney, Agent, or Firm*—Ballard Spahr Andrews & Ingersoll, LLP

(57) ABSTRACT

The invention relates to medicaments for treating cardiac power failure. The medicaments contain a therapeutically effective quantity of one or more S100 protein(s) or one or more mutant or fragments of the same, or contain one or more nucleic acid sequence(s) which code(s) for these amino acid sequences and which are optionally integrated in one or more gene transfer vectors.

20 Claims, 9 Drawing Sheets

SEQUENCE LISTING

```
<160> NUMBER OF SEQ ID NOS: 39

<210> SEQ ID NO 1
<211> LENGTH: 285
<212> TYPE: DNA
<213> ORGANISM: Homo sapiens
<220> FEATURE:
<221> NAME/KEY: CDS
<222> LOCATION: (1)..(282)
<223> OTHER INFORMATION: S100A1 cDNA

<400> SEQUENCE: 1 atg ggc tct gag ctg gag acg gcg atg gag acc ctc atc aac gtg ttc        48
Met Gly Ser Glu Leu Glu Thr Ala Met Glu Thr Leu Ile Asn Val Phe
  1               5                  10                  15 cac gcc cac tcg ggc aaa gag ggg gac aag tac aag ctg agc aag aag        96
His Ala His Ser Gly Lys Glu Gly Asp Lys Tyr Lys Leu Ser Lys Lys
             20                  25                  30 gag ctg aaa gag ctg ctg cag acg gag ctc tct ggc ttc ctg gat gcc       144
Glu Leu Lys Glu Leu Leu Gln Thr Glu Leu Ser Gly Phe Leu Asp Ala
         35                  40                  45 cag aag gat gtg gat gct gtg gac aag gtg atg aag gag cta gac gag       192
Gln Lys Asp Val Asp Ala Val Asp Lys Val Met Lys Glu Leu Asp Glu
     50                  55                  60 aat gga gac ggg gag gtg gac ttc cag gag tat gtg gtg ctt gtg gct       240
Asn Gly Asp Gly Glu Val Asp Phe Gln Glu Tyr Val Val Leu Val Ala
 65                  70                  75                  80 gct ctc aca gtg gcc tgt aac aat ttc ttc tgg gag aac agt tga            285
Ala Leu Thr Val Ala Cys Asn Asn Phe Phe Trp Glu Asn Ser
                 85                  90

<210> SEQ ID NO 2
<211> LENGTH: 94
<212> TYPE: PRT
<213> ORGANISM: Homo sapiens
<223> OTHER INFORMATION: S100A1

<400> SEQUENCE: 2

Met Gly Ser Glu Leu Glu Thr Ala Met Glu Thr Leu Ile Asn Val Phe
  1               5                  10                  15

His Ala His Ser Gly Lys Glu Gly Asp Lys Tyr Lys Leu Ser Lys Lys
             20                  25                  30

Glu Leu Lys Glu Leu Leu Gln Thr Glu Leu Ser Gly Phe Leu Asp Ala
         35                  40                  45

Gln Lys Asp Val Asp Ala Val Asp Lys Val Met Lys Glu Leu Asp Glu
     50                  55                  60

Asn Gly Asp Gly Glu Val Asp Phe Gln Glu Tyr Val Val Leu Val Ala
 65                  70                  75                  80

Ala Leu Thr Val Ala Cys Asn Asn Phe Phe Trp Glu Asn Ser
                 85                  90

<210> SEQ ID NO 3
```

<211> LENGTH: 294
<212> TYPE: DNA
<213> ORGANISM: Homo sapiens
<220> FEATURE:
<221> NAME/KEY: CDS
<222> LOCATION: (1)..(294)
<223> OTHER INFORMATION: S100A2 cDNA

<400> SEQUENCE: 3

```
atg tgc agt tct ctg gag cag gcg ctg gct gtg ctg gtc act acc ttc      48
Met Cys Ser Ser Leu Glu Gln Ala Leu Ala Val Leu Val Thr Thr Phe
 1               5                  10                  15 cac aag tac tcc tgc caa gag ggc gac aag ttc aag ctg agt aag ggg      96
His Lys Tyr Ser Cys Gln Glu Gly Asp Lys Phe Lys Leu Ser Lys Gly
                20                  25                  30 gaa atg aag gaa ctt ctg cac aag gag ctg ccc agc ttt gtg ggg gag     144
Glu Met Lys Glu Leu Leu His Lys Glu Leu Pro Ser Phe Val Gly Glu
         35                  40                  45 aaa gtg gat gag gag ggg ctg aag aag ctg atg ggc agc ctg gat gag     192
Lys Val Asp Glu Glu Gly Leu Lys Lys Leu Met Gly Ser Leu Asp Glu
 50                  55                  60 aac agt gac cag cag gtg gac ttc cag gag tat gct gtt ttc ctg gca     240
Asn Ser Asp Gln Gln Val Asp Phe Gln Glu Tyr Ala Val Phe Leu Ala
 65                  70                  75                  80 ctc atc act gtc atg tgc aat gac ttc ttc cag ggc tgc cca gac cga     288
Leu Ile Thr Val Met Cys Asn Asp Phe Phe Gln Gly Cys Pro Asp Arg
                 85                  90                  95 ccc tga                                                              294
Pro
```

<210> SEQ ID NO 4
<211> LENGTH: 97
<212> TYPE: PRT
<213> ORGANISM: Homo sapiens
<223> OTHER INFORMATION: S100A2

<400> SEQUENCE: 4

```
Met Cys Ser Ser Leu Glu Gln Ala Leu Ala Val Leu Val Thr Thr Phe
 1               5                  10                  15

His Lys Tyr Ser Cys Gln Glu Gly Asp Lys Phe Lys Leu Ser Lys Gly
                20                  25                  30

Glu Met Lys Glu Leu Leu His Lys Glu Leu Pro Ser Phe Val Gly Glu
         35                  40                  45

Lys Val Asp Glu Glu Gly Leu Lys Lys Leu Met Gly Ser Leu Asp Glu
 50                  55                  60

Asn Ser Asp Gln Gln Val Asp Phe Gln Glu Tyr Ala Val Phe Leu Ala
 65                  70                  75                  80

Leu Ile Thr Val Met Cys Asn Asp Phe Phe Gln Gly Cys Pro Asp Arg
                 85                  90                  95

Pro
```

<210> SEQ ID NO 5
<211> LENGTH: 306
<212> TYPE: DNA
<213> ORGANISM: Homo sapiens
<220> FEATURE:
<221> NAME/KEY: CDS
<222> LOCATION: (1)..(306)
<223> OTHER INFORMATION: S100A3 cDNA

<400> SEQUENCE: 5

```
atg gcc agg cct ctg gag cag gcg gta gct gcc atc gtg tgc acc ttc      48
```

```
Met Ala Arg Pro Leu Glu Gln Ala Val Ala Ile Val Cys Thr Phe
  1               5                  10                  15 cag gaa tac gca ggg cgc tgt ggg gac aaa tac aag ctc tgc cag gcg         96
Gln Glu Tyr Ala Gly Arg Cys Gly Asp Lys Tyr Lys Leu Cys Gln Ala
                20                  25                  30 gag ctc aag gag ctg ctg cag aag gag ctg gcc acc tgg acc ccg act        144
Glu Leu Lys Glu Leu Leu Gln Lys Glu Leu Ala Thr Trp Thr Pro Thr
         35                  40                  45 gag ttt cgg gaa tgt gac tac aac aaa ttc atg agt gtt ctg gac acc        192
Glu Phe Arg Glu Cys Asp Tyr Asn Lys Phe Met Ser Val Leu Asp Thr
     50                  55                  60 aac aag gac tgc gag gtg gac ttt gtg gag tat gtg cgc tca ctt gcc        240
Asn Lys Asp Cys Glu Val Asp Phe Val Glu Tyr Val Arg Ser Leu Ala
 65                  70                  75                  80 tgc ctc tgt ctc tac tgc cac gag tac ttc aag gac tgc ccc tca gag        288
Cys Leu Cys Leu Tyr Cys His Glu Tyr Phe Lys Asp Cys Pro Ser Glu
                 85                  90                  95 ccc ccc tgc tcc cag tag                                                306
Pro Pro Cys Ser Gln
            100
```

```
<210> SEQ ID NO 6
<211> LENGTH: 101
<212> TYPE: PRT
<213> ORGANISM: Homo sapiens
<223> OTHER INFORMATION: S100A3

<400> SEQUENCE: 6

Met Ala Arg Pro Leu Glu Gln Ala Val Ala Ile Val Cys Thr Phe
  1               5                  10                  15

Gln Glu Tyr Ala Gly Arg Cys Gly Asp Lys Tyr Lys Leu Cys Gln Ala
                20                  25                  30

Glu Leu Lys Glu Leu Leu Gln Lys Glu Leu Ala Thr Trp Thr Pro Thr
         35                  40                  45

Glu Phe Arg Glu Cys Asp Tyr Asn Lys Phe Met Ser Val Leu Asp Thr
     50                  55                  60

Asn Lys Asp Cys Glu Val Asp Phe Val Glu Tyr Val Arg Ser Leu Ala
 65                  70                  75                  80

Cys Leu Cys Leu Tyr Cys His Glu Tyr Phe Lys Asp Cys Pro Ser Glu
                 85                  90                  95

Pro Pro Cys Ser Gln
            100
```

```
<210> SEQ ID NO 7
<211> LENGTH: 306
<212> TYPE: DNA
<213> ORGANISM: Homo sapiens
<220> FEATURE:
<221> NAME/KEY: CDS
<222> LOCATION: (1)..(306)
<223> OTHER INFORMATION: S100A4 cDNA

<400> SEQUENCE: 7 atg gcg tgc cct ctg gag aag gcc ctg gat gtg atg gtg tcc acc ttc         48
Met Ala Cys Pro Leu Glu Lys Ala Leu Asp Val Met Val Ser Thr Phe
  1               5                  10                  15 cac aag tac tcg ggc aaa gag ggt gac aag ttc aag ctc aac aag tca         96
His Lys Tyr Ser Gly Lys Glu Gly Asp Lys Phe Lys Leu Asn Lys Ser
                20                  25                  30 gaa cta aag gag ctg ctg acc cgg gag ctg ccc agc ttc ttg ggg aaa        144
Glu Leu Lys Glu Leu Leu Thr Arg Glu Leu Pro Ser Phe Leu Gly Lys
```

```
                 35                  40                  45
agg aca gat gaa gct gct ttc cag aag ctg atg agc aac ttg gac agc       192
Arg Thr Asp Glu Ala Ala Phe Gln Lys Leu Met Ser Asn Leu Asp Ser
     50                  55                  60 aac agg gac aac gag gtg gac ttc caa gag tac tgt gtc ttc ctg tcc       240
Asn Arg Asp Asn Glu Val Asp Phe Gln Glu Tyr Cys Val Phe Leu Ser
 65                  70                  75                  80 tgc atc gcc atg atg tgt aac gaa ttc ttt gaa ggc ttc cca gat aag       288
Cys Ile Ala Met Met Cys Asn Glu Phe Phe Glu Gly Phe Pro Asp Lys
                 85                  90                  95 cag ccc agg aag aaa tga                                               306
Gln Pro Arg Lys Lys
            100

<210> SEQ ID NO 8
<211> LENGTH: 101
<212> TYPE: PRT
<213> ORGANISM: Homo sapiens
<223> OTHER INFORMATION: S100A4

<400> SEQUENCE: 8

Met Ala Cys Pro Leu Glu Lys Ala Leu Asp Val Met Val Ser Thr Phe
 1               5                  10                  15

His Lys Tyr Ser Gly Lys Glu Gly Asp Lys Phe Lys Leu Asn Lys Ser
                 20                  25                  30

Glu Leu Lys Glu Leu Leu Thr Arg Glu Leu Pro Ser Phe Leu Gly Lys
             35                  40                  45

Arg Thr Asp Glu Ala Ala Phe Gln Lys Leu Met Ser Asn Leu Asp Ser
     50                  55                  60

Asn Arg Asp Asn Glu Val Asp Phe Gln Glu Tyr Cys Val Phe Leu Ser
 65                  70                  75                  80

Cys Ile Ala Met Met Cys Asn Glu Phe Phe Glu Gly Phe Pro Asp Lys
                 85                  90                  95

Gln Pro Arg Lys Lys
            100

<210> SEQ ID NO 9
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: S100A5 cDNA

<400> SEQUENCE: 9 atg cct gct gct tgg att ctc tgg gct cac tcc cac agt gag ctg cac        48
Met Pro Ala Ala Trp Ile Leu Trp Ala His Ser His Ser Glu Leu His
 1               5                  10                  15 act gtg atg gag act cct ctg gag aag gcc ctg acc act atg gtg acc        96
Thr Val Met Glu Thr Pro Leu Glu Lys Ala Leu Thr Thr Met Val Thr
                 20                  25                  30 acg ttt cac aaa tat tcg ggg aga gag ggt agc aaa ctg acc ctg agt       144
Thr Phe His Lys Tyr Ser Gly Arg Glu Gly Ser Lys Leu Thr Leu Ser
             35                  40                  45 agg aag gaa ctc aag gag ctg atc aag aaa gag ctg tgt ctt ggg gag       192
Arg Lys Glu Leu Lys Glu Leu Ile Lys Lys Glu Leu Cys Leu Gly Glu
     50                  55                  60 atg aag gag agc agc atc gat gac ttg atg aag agc ctg gac aag aac       240
Met Lys Glu Ser Ser Ile Asp Asp Leu Met Lys Ser Leu Asp Lys Asn
 65                  70                  75                  80
```

```
agc gac cag gag atc gac ttc aag gag tac tcg gtg ttc ctg acc atg      288
Ser Asp Gln Glu Ile Asp Phe Lys Glu Tyr Ser Val Phe Leu Thr Met
                85                  90                  95 ctg tgc atg gcc tac aac gac ttc ttt cta gag gac aac aag tga          333
Leu Cys Met Ala Tyr Asn Asp Phe Phe Leu Glu Asp Asn Lys
            100                 105                 110

<210> SEQ ID NO 10
<211> LENGTH: 110
<212> TYPE: PRT
<213> ORGANISM: Homo sapiens
<223> OTHER INFORMATION: S100A5

<400> SEQUENCE: 10

Met Pro Ala Ala Trp Ile Leu Trp Ala His Ser His Ser Glu Leu His
  1               5                  10                  15

Thr Val Met Glu Thr Pro Leu Glu Lys Ala Leu Thr Thr Met Val Thr
                20                  25                  30

Thr Phe His Lys Tyr Ser Gly Arg Glu Gly Ser Lys Leu Thr Leu Ser
            35                  40                  45

Arg Lys Glu Leu Lys Glu Leu Ile Lys Lys Glu Leu Cys Leu Gly Glu
 50                  55                  60

Met Lys Glu Ser Ser Ile Asp Asp Leu Met Lys Ser Leu Asp Lys Asn
 65                  70                  75                  80

Ser Asp Gln Glu Ile Asp Phe Lys Glu Tyr Ser Val Phe Leu Thr Met
                85                  90                  95

Leu Cys Met Ala Tyr Asn Asp Phe Phe Leu Glu Asp Asn Lys
            100                 105                 110

<210> SEQ ID NO 11
<211> LENGTH: 273
<212> TYPE: DNA
<213> ORGANISM: Homo sapiens
<220> FEATURE:
<221> NAME/KEY: CDS
<222> LOCATION: (1)..(273)
<223> OTHER INFORMATION: S100A6 cDNA

<400> SEQUENCE: 11 atg gca tgc ccc ctg gat cag gcc att ggc ctc ctc gtg gcc atc ttc      48
Met Ala Cys Pro Leu Asp Gln Ala Ile Gly Leu Leu Val Ala Ile Phe
  1               5                  10                  15 cac aag tac tcc ggc agg gag ggt gac aag cac acc ctg agc aag aag      96
His Lys Tyr Ser Gly Arg Glu Gly Asp Lys His Thr Leu Ser Lys Lys
                20                  25                  30 gag ctg aag gag ctg atc cag aag gag ctc acc att ggc tcg aag ctg     144
Glu Leu Lys Glu Leu Ile Gln Lys Glu Leu Thr Ile Gly Ser Lys Leu
            35                  40                  45 cag gat gct gaa att gca agg ctg atg gaa gac ttg gac cgg aac aag     192
Gln Asp Ala Glu Ile Ala Arg Leu Met Glu Asp Leu Asp Arg Asn Lys
 50                  55                  60 gac cag gag gtg aac ttc cag gag tat gtc acc ttc ctg ggg gcc ttg     240
Asp Gln Glu Val Asn Phe Gln Glu Tyr Val Thr Phe Leu Gly Ala Leu
 65                  70                  75                  80 gct ttg atc tac aat gaa gcc ctc aag ggc tga                         273
Ala Leu Ile Tyr Asn Glu Ala Leu Lys Gly
                85                  90

<210> SEQ ID NO 12
<211> LENGTH: 90
<212> TYPE: PRT
```

<213> ORGANISM: Homo sapiens
<223> OTHER INFORMATION: S100A6

<400> SEQUENCE: 12

Met Ala Cys Pro Leu Asp Gln Ala Ile Gly Leu Leu Val Ala Ile Phe
1               5                   10                  15

His Lys Tyr Ser Gly Arg Glu Gly Asp Lys His Thr Leu Ser Lys Lys
            20                  25                  30

Glu Leu Lys Glu Leu Ile Gln Lys Glu Leu Thr Ile Gly Ser Lys Leu
        35                  40                  45

Gln Asp Ala Glu Ile Ala Arg Leu Met Glu Asp Leu Asp Arg Asn Lys
    50                  55                  60

Asp Gln Glu Val Asn Phe Gln Glu Tyr Val Thr Phe Leu Gly Ala Leu
65                  70                  75                  80

Ala Leu Ile Tyr Asn Glu Ala Leu Lys Gly
                85                  90

<210> SEQ ID NO 13
<211> LENGTH: 306
<212> TYPE: DNA
<213> ORGANISM: Homo sapiens
<220> FEATURE:
<221> NAME/KEY: CDS
<222> LOCATION: (1)..(306)
<223> OTHER INFORMATION: S100A7 cDNA

<400> SEQUENCE: 13 atg agc aac act caa gct gag agg tcc ata ata ggc atg atc gac atg      48
Met Ser Asn Thr Gln Ala Glu Arg Ser Ile Ile Gly Met Ile Asp Met
1               5                   10                  15 ttt cac aaa tac acc aga cgt gat gac aag att gac aag cca agc ctg      96
Phe His Lys Tyr Thr Arg Arg Asp Asp Lys Ile Asp Lys Pro Ser Leu
            20                  25                  30 ctg acg atg atg aag gag aac ttc ccc aac ttc ctt agt gcc tgt gac     144
Leu Thr Met Met Lys Glu Asn Phe Pro Asn Phe Leu Ser Ala Cys Asp
        35                  40                  45 aaa aag ggc aca aat tac ctc gcc gac gtc ttt gag aaa aag gac aag     192
Lys Lys Gly Thr Asn Tyr Leu Ala Asp Val Phe Glu Lys Lys Asp Lys
    50                  55                  60 aat gag gat aag aag att gat ttt tct gag ttt ctg tcc ttg ctg gga     240
Asn Glu Asp Lys Lys Ile Asp Phe Ser Glu Phe Leu Ser Leu Leu Gly
65                  70                  75                  80 gac ata gcc aca gac tac cac aag cag agc cat gga gca gcg ccc tgt     288
Asp Ile Ala Thr Asp Tyr His Lys Gln Ser His Gly Ala Ala Pro Cys
                85                  90                  95 tcc ggg ggc agc cag tga                                              306
Ser Gly Gly Ser Gln
            100

<210> SEQ ID NO 14
<211> LENGTH: 101
<212> TYPE: PRT
<213> ORGANISM: Homo sapiens
<223> OTHER INFORMATION: S100A7

<400> SEQUENCE: 14

Met Ser Asn Thr Gln Ala Glu Arg Ser Ile Ile Gly Met Ile Asp Met
1               5                   10                  15

Phe His Lys Tyr Thr Arg Arg Asp Asp Lys Ile Asp Lys Pro Ser Leu
            20                  25                  30

Leu Thr Met Met Lys Glu Asn Phe Pro Asn Phe Leu Ser Ala Cys Asp

```
                35                  40                  45
Lys Lys Gly Thr Asn Tyr Leu Ala Asp Val Phe Glu Lys Lys Asp Lys
 50                  55                  60

Asn Glu Asp Lys Lys Ile Asp Phe Ser Glu Phe Leu Ser Leu Leu Gly
 65                  70                  75                  80

Asp Ile Ala Thr Asp Tyr His Lys Gln Ser His Gly Ala Ala Pro Cys
                 85                  90                  95

Ser Gly Gly Ser Gln
            100

<210> SEQ ID NO 15
<211> LENGTH: 282
<212> TYPE: DNA
<213> ORGANISM: Homo sapiens
<220> FEATURE:
<221> NAME/KEY: CDS
<222> LOCATION: (1)..(282)
<223> OTHER INFORMATION: S100A8 cDNA

<400> SEQUENCE: 15 atg ttg acc gag ctg gag aaa gcc ttg aac tct atc atc gac gtc tac    48
Met Leu Thr Glu Leu Glu Lys Ala Leu Asn Ser Ile Ile Asp Val Tyr
  1               5                  10                  15 cac aag tac tcc ctg ata aag ggg aat ttc cat gcc gtc tac agg gat    96
His Lys Tyr Ser Leu Ile Lys Gly Asn Phe His Ala Val Tyr Arg Asp
                 20                  25                  30 gac ctg aag aaa ttg cta gag acc gag tgt cct cag tat atc agg aaa   144
Asp Leu Lys Lys Leu Leu Glu Thr Glu Cys Pro Gln Tyr Ile Arg Lys
             35                  40                  45 aag ggt gca gac gtc tgg ttc aaa gag ttg gat atc aac act gat ggt   192
Lys Gly Ala Asp Val Trp Phe Lys Glu Leu Asp Ile Asn Thr Asp Gly
 50                  55                  60 gca gtt aac ttc cag gag ttc ctc att ctg gtg ata aag atg ggc gtg   240
Ala Val Asn Phe Gln Glu Phe Leu Ile Leu Val Ile Lys Met Gly Val
 65                  70                  75                  80 gca gcc cac aaa aaa agc cat gaa gaa agc cac aaa gag tag           282
Ala Ala His Lys Lys Ser His Glu Glu Ser His Lys Glu
                 85                  90

<210> SEQ ID NO 16
<211> LENGTH: 93
<212> TYPE: PRT
<213> ORGANISM: Homo sapiens
<223> OTHER INFORMATION: S100A8

<400> SEQUENCE: 16

Met Leu Thr Glu Leu Glu Lys Ala Leu Asn Ser Ile Ile Asp Val Tyr
  1               5                  10                  15

His Lys Tyr Ser Leu Ile Lys Gly Asn Phe His Ala Val Tyr Arg Asp
                 20                  25                  30

Asp Leu Lys Lys Leu Leu Glu Thr Glu Cys Pro Gln Tyr Ile Arg Lys
             35                  40                  45

Lys Gly Ala Asp Val Trp Phe Lys Glu Leu Asp Ile Asn Thr Asp Gly
 50                  55                  60

Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90

<210> SEQ ID NO 17
```

```
<211> LENGTH: 345
<212> TYPE: DNA
<213> ORGANISM: Homo sapiens
<220> FEATURE:
<221> NAME/KEY: CDS
<222> LOCATION: (1)..(342)
<223> OTHER INFORMATION: S100A9 cDNA

<400> SEQUENCE: 17 atg act tgc aaa atg tcg cag ctg gaa cgc aac ata gag acc atc atc      48
Met Thr Cys Lys Met Ser Gln Leu Glu Arg Asn Ile Glu Thr Ile Ile
1               5                  10                  15 aac acc ttc cac caa tac tct gtg aag ctg ggg cac cca gac acc ctg      96
Asn Thr Phe His Gln Tyr Ser Val Lys Leu Gly His Pro Asp Thr Leu
            20                  25                  30 aac cag ggg gaa ttc aaa gag ctg gtg cga aaa gat ctg caa aat ttt     144
Asn Gln Gly Glu Phe Lys Glu Leu Val Arg Lys Asp Leu Gln Asn Phe
        35                  40                  45 ctc aag aag gag aat aag aat gaa aag gtc ata gaa cac atc atg gag     192
Leu Lys Lys Glu Asn Lys Asn Glu Lys Val Ile Glu His Ile Met Glu
    50                  55                  60 gac ctg gac aca aat gca gac aag cag ctg agc ttc gag gag ttc atc     240
Asp Leu Asp Thr Asn Ala Asp Lys Gln Leu Ser Phe Glu Glu Phe Ile
65                  70                  75                  80 atg ctg atg gcg agg cta acc tgg gcc tcc cac gag aag atg cac gag     288
Met Leu Met Ala Arg Leu Thr Trp Ala Ser His Glu Lys Met His Glu
                85                  90                  95 ggt gac gag ggc cct ggc cac cac cat aag cca ggc ctc ggg gag ggc     336
Gly Asp Glu Gly Pro Gly His His His Lys Pro Gly Leu Gly Glu Gly
            100                 105                 110 acc ccc taa                                                         345
Thr Pro

<210> SEQ ID NO 18
<211> LENGTH: 114
<212> TYPE: PRT
<213> ORGANISM: Homo sapiens
<223> OTHER INFORMATION: S100A9

<400> SEQUENCE: 18

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 19
<211> LENGTH: 294
<212> TYPE: DNA
<213> ORGANISM: Homo sapiens
<220> FEATURE:
```

<221> NAME/KEY: CDS
<222> LOCATION: (1)..(294)
<223> OTHER INFORMATION: S100A10 cDNA

<400> SEQUENCE: 19

```
atg cca tct caa atg gaa cac gcc atg gaa acc atg atg ttt aca ttt    48
Met Pro Ser Gln Met Glu His Ala Met Glu Thr Met Met Phe Thr Phe
 1               5                  10                  15 cac aaa ttc gct ggg gat aaa ggc tac tta aca aag gag gac ctg aga    96
His Lys Phe Ala Gly Asp Lys Gly Tyr Leu Thr Lys Glu Asp Leu Arg
             20                  25                  30 gta ctc atg gaa aag gag ttc cct gga ttt ttg gaa aat caa aaa gac   144
Val Leu Met Glu Lys Glu Phe Pro Gly Phe Leu Glu Asn Gln Lys Asp
         35                  40                  45 cct ctg gct gtg gac aaa ata atg aag gac ctg gac cag tgt aga gat   192
Pro Leu Ala Val Asp Lys Ile Met Lys Asp Leu Asp Gln Cys Arg Asp
     50                  55                  60 ggc aaa gtg ggc ttc cag agc ttc ttt tcc cta att gcg ggc ctc acc   240
Gly Lys Val Gly Phe Gln Ser Phe Phe Ser Leu Ile Ala Gly Leu Thr
 65                  70                  75                  80 att gca tgc aat gac tat ttt gta gta cac atg aag cag aag gga aag   288
Ile Ala Cys Asn Asp Tyr Phe Val Val His Met Lys Gln Lys Gly Lys
                 85                  90                  95 aag tag                                                            294
Lys
```

<210> SEQ ID NO 20
<211> LENGTH: 97
<212> TYPE: PRT
<213> ORGANISM: Homo sapiens
<223> OTHER INFORMATION: S100A10

<400> SEQUENCE: 20

```
Met Pro Ser Gln Met Glu His Ala Met Glu Thr Met Met Phe Thr Phe
 1               5                  10                  15

His Lys Phe Ala Gly Asp Lys Gly Tyr Leu Thr Lys Glu Asp Leu Arg
             20                  25                  30

Val Leu Met Glu Lys Glu Phe Pro Gly Phe Leu Glu Asn Gln Lys Asp
         35                  40                  45

Pro Leu Ala Val Asp Lys Ile Met Lys Asp Leu Asp Gln Cys Arg Asp
     50                  55                  60

Gly Lys Val Gly Phe Gln Ser Phe Phe Ser Leu Ile Ala Gly Leu Thr
 65                  70                  75                  80

Ile Ala Cys Asn Asp Tyr Phe Val Val His Met Lys Gln Lys Gly Lys
                 85                  90                  95

Lys
```

<210> SEQ ID NO 21
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: S100A11 cDNA

<400> SEQUENCE: 21

```
atg gca aaa atc tcc agc cct aca gag act gag cgg tgc atc gag tcc    48
Met Ala Lys Ile Ser Ser Pro Thr Glu Thr Glu Arg Cys Ile Glu Ser
 1               5                  10                  15 ctg att gct gtc ttc cag aag tat gct gga aag gat ggt tat aac tac    96
Leu Ile Ala Val Phe Gln Lys Tyr Ala Gly Lys Asp Gly Tyr Asn Tyr
```

```
Leu Ile Ala Val Phe Gln Lys Tyr Ala Gly Lys Asp Gly Tyr Asn Tyr
            20                  25                  30 act ctc tcc aag aca gag ttc cta agc ttc atg aat aca gaa cta gct      144
Thr Leu Ser Lys Thr Glu Phe Leu Ser Phe Met Asn Thr Glu Leu Ala
            35                  40                  45 gcc ttc aca aag aac cag aag gac cct ggt gtc ctt gac cgc atg atg      192
Ala Phe Thr Lys Asn Gln Lys Asp Pro Gly Val Leu Asp Arg Met Met
    50                  55                  60 aag aaa ctg gac acc aac agt gat ggt cag cta gat ttc tca gaa ttt      240
Lys Lys Leu Asp Thr Asn Ser Asp Gly Gln Leu Asp Phe Ser Glu Phe
65                  70                  75                  80 ctt aat ctg att ggt ggc cta gct atg gct tgc cat gac tcc ttc ctc      288
Leu Asn Leu Ile Gly Gly Leu Ala Met Ala Cys His Asp Ser Phe Leu
                85                  90                  95 aag gct gtc cct tcc cag aag cgg acc tga                              318
Lys Ala Val Pro Ser Gln Lys Arg Thr
                100             105
```

```
<210> SEQ ID NO 22
<211> LENGTH: 105
<212> TYPE: PRT
<213> ORGANISM: Homo sapiens
<223> OTHER INFORMATION: S100A11

<400> SEQUENCE: 22

Met Ala Lys Ile Ser Ser Pro Thr Glu Thr Glu Arg Cys Ile Glu Ser
1               5                   10                  15

Leu Ile Ala Val Phe Gln Lys Tyr Ala Gly Lys Asp Gly Tyr Asn Tyr
            20                  25                  30

Thr Leu Ser Lys Thr Glu Phe Leu Ser Phe Met Asn Thr Glu Leu Ala
            35                  40                  45

Ala Phe Thr Lys Asn Gln Lys Asp Pro Gly Val Leu Asp Arg Met Met
    50                  55                  60

Lys Lys Leu Asp Thr Asn Ser Asp Gly Gln Leu Asp Phe Ser Glu Phe
65                  70                  75                  80

Leu Asn Leu Ile Gly Gly Leu Ala Met Ala Cys His Asp Ser Phe Leu
                85                  90                  95

Lys Ala Val Pro Ser Gln Lys Arg Thr
                100             105

<210> SEQ ID NO 23
<211> LENGTH: 279
<212> TYPE: DNA
<213> ORGANISM: Homo sapiens
<220> FEATURE:
<221> NAME/KEY: CDS
<222> LOCATION: (1)..(279)
<223> OTHER INFORMATION: S100A12 cDNA

<400> SEQUENCE: 23 atg aca aaa ctt gaa gag cat ctg gag gga att gtc aat atc ttc cac      48
Met Thr Lys Leu Glu Glu His Leu Glu Gly Ile Val Asn Ile Phe His
1               5                   10                  15 caa tac tca gtt cgg aag ggg cat ttt gac acc ctc tct aag ggt gag      96
Gln Tyr Ser Val Arg Lys Gly His Phe Asp Thr Leu Ser Lys Gly Glu
            20                  25                  30 ctg aag cag ctg ctt aca aag gag ctt gca aac acc atc aag aat atc      144
Leu Lys Gln Leu Leu Thr Lys Glu Leu Ala Asn Thr Ile Lys Asn Ile
            35                  40                  45 aaa gat aaa gct gtc att gat gaa ata ttc caa ggc ctg gat gct aat      192
Lys Asp Lys Ala Val Ile Asp Glu Ile Phe Gln Gly Leu Asp Ala Asn
    50                  55                  60
```

```
                50                     55                    60
caa gat gaa cag gtc gac ttt caa gaa ttc ata tcc ctg gta gcc att         240
Gln Asp Glu Gln Val Asp Phe Gln Glu Phe Ile Ser Leu Val Ala Ile
 65                  70                  75                  80 gcg ctg aag gct gcc cat tac cac acc cac aaa gag tag                     279
Ala Leu Lys Ala Ala His Tyr His Thr His Lys Glu
                 85                  90

<210> SEQ ID NO 24
<211> LENGTH: 92
<212> TYPE: PRT
<213> ORGANISM: Homo sapiens
<223> OTHER INFORMATION: S100A12

<400> SEQUENCE: 24

Met Thr Lys Leu Glu Glu His Leu Glu Gly Ile Val Asn Ile Phe His
 1               5                  10                  15

Gln Tyr Ser Val Arg Lys Gly His Phe Asp Thr Leu Ser Lys Gly Glu
                20                  25                  30

Leu Lys Gln Leu Leu Thr Lys Glu Leu Ala Asn Thr Ile Lys Asn Ile
         35                  40                  45

Lys Asp Lys Ala Val Ile Asp Glu Ile Phe Gln Gly Leu Asp Ala Asn
     50                  55                  60

Gln Asp Glu Gln Val Asp Phe Gln Glu Phe Ile Ser Leu Val Ala Ile
 65                  70                  75                  80

Ala Leu Lys Ala Ala His Tyr His Thr His Lys Glu
                 85                  90

<210> SEQ ID NO 25
<211> LENGTH: 297
<212> TYPE: DNA
<213> ORGANISM: Homo sapiens
<220> FEATURE:
<221> NAME/KEY: CDS
<222> LOCATION: (1)..(297)
<223> OTHER INFORMATION: S100A13 cDNA

<400> SEQUENCE: 25 atg gca gca gaa cca ctg aca gag cta gag gag tcc att gag acc gtg          48
Met Ala Ala Glu Pro Leu Thr Glu Leu Glu Glu Ser Ile Glu Thr Val
 1               5                  10                  15 gtc acc acc ttc ttc acc ttt gca agg cag gag ggc cgg aag gat agc          96
Val Thr Thr Phe Phe Thr Phe Ala Arg Gln Glu Gly Arg Lys Asp Ser
                20                  25                  30 ctc agc gtc aac gag ttc aaa gag ctg gtt acc cag cag ttg ccc cat         144
Leu Ser Val Asn Glu Phe Lys Glu Leu Val Thr Gln Gln Leu Pro His
         35                  40                  45 ctg ctc aag gat gtg ggc tct ctt gat gag aag atg aag agc ttg gat         192
Leu Leu Lys Asp Val Gly Ser Leu Asp Glu Lys Met Lys Ser Leu Asp
     50                  55                  60 gtg aat cag gac tcg gag ctc aag ttc aat gag tac tgg aga ttg att         240
Val Asn Gln Asp Ser Glu Leu Lys Phe Asn Glu Tyr Trp Arg Leu Ile
 65                  70                  75                  80 ggg gag ctg gcc aag gaa atc agg aag aag aaa gac ctg aag atc agg         288
Gly Glu Leu Ala Lys Glu Ile Arg Lys Lys Lys Asp Leu Lys Ile Arg
                 85                  90                  95 aag aag taa                                                             297
Lys Lys

<210> SEQ ID NO 26
<211> LENGTH: 98
```

```
<212> TYPE: PRT
<213> ORGANISM: Homo sapiens
<223> OTHER INFORMATION: S100A13

<400> SEQUENCE: 26

Met Ala Ala Glu Pro Leu Thr Glu Leu Glu Glu Ser Ile Glu Thr Val
 1               5                  10                  15

Val Thr Thr Phe Phe Thr Phe Ala Arg Gln Glu Gly Arg Lys Asp Ser
                20                  25                  30

Leu Ser Val Asn Glu Phe Lys Glu Leu Val Thr Gln Gln Leu Pro His
            35                  40                  45

Leu Leu Lys Asp Val Gly Ser Leu Asp Glu Lys Met Lys Ser Leu Asp
        50                  55                  60

Val Asn Gln Asp Ser Glu Leu Lys Phe Asn Glu Tyr Trp Arg Leu Ile
 65                  70                  75                  80

Gly Glu Leu Ala Lys Glu Ile Arg Lys Lys Asp Leu Lys Ile Arg
                85                  90                  95

Lys Lys

<210> SEQ ID NO 27
<211> LENGTH: 288
<212> TYPE: DNA
<213> ORGANISM: Homo sapiens
<220> FEATURE:
<221> NAME/KEY: CDS
<222> LOCATION: (1)..(288)
<223> OTHER INFORMATION: S100B cDNA

<400> SEQUENCE: 27 atg acg gaa cta gag aca gcc atg ggc atg atc ata gac gtc ttt tcc        48
Met Thr Glu Leu Glu Thr Ala Met Gly Met Ile Ile Asp Val Phe Ser
 1               5                  10                  15 cga tat tcg ggc agc gag ggc agc acg cag acc ctg acc aag ggg gag        96
Arg Tyr Ser Gly Ser Glu Gly Ser Thr Gln Thr Leu Thr Lys Gly Glu
                20                  25                  30 ctc aag gtg ctg atg gag aag gag cta cca ggc ttc ctg cag agt gga       144
Leu Lys Val Leu Met Glu Lys Glu Leu Pro Gly Phe Leu Gln Ser Gly
            35                  40                  45 aaa gac aag gat gcc gtg gat aaa ttg ctc aag gac ctg gac gcc aat       192
Lys Asp Lys Asp Ala Val Asp Lys Leu Leu Lys Asp Leu Asp Ala Asn
        50                  55                  60 gga gat gcc cag gtg gac ttc agt gag ttc atc gtg ttc gtg gct gca       240
Gly Asp Ala Gln Val Asp Phe Ser Glu Phe Ile Val Phe Val Ala Ala
 65                  70                  75                  80 atc acg tct gcc tgt cac aag tac ttt gag aag gca gga ctc aaa tga       288
Ile Thr Ser Ala Cys His Lys Tyr Phe Glu Lys Ala Gly Leu Lys
                85                  90                  95

<210> SEQ ID NO 28
<211> LENGTH: 95
<212> TYPE: PRT
<213> ORGANISM: Homo sapiens
<223> OTHER INFORMATION: S100B

<400> SEQUENCE: 28

Met Thr Glu Leu Glu Thr Ala Met Gly Met Ile Ile Asp Val Phe Ser
 1               5                  10                  15

Arg Tyr Ser Gly Ser Glu Gly Ser Thr Gln Thr Leu Thr Lys Gly Glu
                20                  25                  30

Leu Lys Val Leu Met Glu Lys Glu Leu Pro Gly Phe Leu Gln Ser Gly
            35                  40                  45
```

-continued

```
Lys Asp Lys Asp Ala Val Asp Lys Leu Leu Lys Asp Leu Asp Ala Asn
         50                  55                  60

Gly Asp Ala Gln Val Asp Phe Ser Glu Phe Ile Val Phe Val Ala Ala
 65                  70                  75                  80

Ile Thr Ser Ala Cys His Lys Tyr Phe Glu Lys Ala Gly Leu Lys
                 85                  90                  95

<210> SEQ ID NO 29
<211> LENGTH: 288
<212> TYPE: DNA
<213> ORGANISM: Homo sapiens
<220> FEATURE:
<221> NAME/KEY: CDS
<222> LOCATION: (1)..(288)
<223> OTHER INFORMATION: S100P cDNA

<400> SEQUENCE: 29 atg acg gaa cta gag aca gcc atg ggc atg atc ata gac gtc ttt tcc      48
Met Thr Glu Leu Glu Thr Ala Met Gly Met Ile Ile Asp Val Phe Ser
 1               5                  10                  15 cga tat tcg ggc agc gag ggc agc acg cag acc ctg acc aag ggg gag      96
Arg Tyr Ser Gly Ser Glu Gly Ser Thr Gln Thr Leu Thr Lys Gly Glu
             20                  25                  30 ctc aag gtg ctg atg gag aag gag cta cca ggc ttc ctg cag agt gga     144
Leu Lys Val Leu Met Glu Lys Glu Leu Pro Gly Phe Leu Gln Ser Gly
         35                  40                  45 aaa gac aag gat gcc gtg gat aaa ttg ctc aag gac ctg gac gcc aat     192
Lys Asp Lys Asp Ala Val Asp Lys Leu Leu Lys Asp Leu Asp Ala Asn
     50                  55                  60 gga gat gcc cag gtg gac ttc agt gag ttc atc gtg ttc gtg gct gca     240
Gly Asp Ala Gln Val Asp Phe Ser Glu Phe Ile Val Phe Val Ala Ala
 65                  70                  75                  80 atc acg tct gcc tgt cac aag tac ttt gag aag gca gga ctc aaa tga     288
Ile Thr Ser Ala Cys His Lys Tyr Phe Glu Lys Ala Gly Leu Lys
                 85                  90                  95

<210> SEQ ID NO 30
<211> LENGTH: 95
<212> TYPE: PRT
<213> ORGANISM: Homo sapiens
<223> OTHER INFORMATION: S100P

<400> SEQUENCE: 30

Met Thr Glu Leu Glu Thr Ala Met Gly Met Ile Ile Asp Val Phe Ser
 1               5                  10                  15

Arg Tyr Ser Gly Ser Glu Gly Ser Thr Gln Thr Leu Thr Lys Gly Glu
             20                  25                  30

Leu Lys Val Leu Met Glu Lys Glu Leu Pro Gly Phe Leu Gln Ser Gly
         35                  40                  45

Lys Asp Lys Asp Ala Val Asp Lys Leu Leu Lys Asp Leu Asp Ala Asn
     50                  55                  60

Gly Asp Ala Gln Val Asp Phe Ser Glu Phe Ile Val Phe Val Ala Ala
 65                  70                  75                  80

Ile Thr Ser Ala Cys His Lys Tyr Phe Glu Lys Ala Gly Leu Lys
                 85                  90                  95

<210> SEQ ID NO 31
<211> LENGTH: 45
<212> TYPE: DNA
<213> ORGANISM: Homo sapiens
<220> FEATURE:
```

```
<221> NAME/KEY: CDS
<222> LOCATION: (1)..(45)
<223> OTHER INFORMATION: S100A1 cDNA [N-terminal]

<400> SEQUENCE: 31 ggc tct gag ctg gag acg gcg atg gag acc ctc atc aac gtg ttc       45
Gly Ser Glu Leu Glu Thr Ala Met Glu Thr Leu Ile Asn Val Phe
 1               5                  10                  15

<210> SEQ ID NO 32
<211> LENGTH: 15
<212> TYPE: PRT
<213> ORGANISM: Homo sapiens
<223> OTHER INFORMATION: S100A1 [N-terminal]

<400> SEQUENCE: 32

Gly Ser Glu Leu Glu Thr Ala Met Glu Thr Leu Ile Asn Val Phe
 1               5                  10                  15

<210> SEQ ID NO 33
<211> LENGTH: 39
<212> TYPE: DNA
<213> ORGANISM: Homo sapiens
<220> FEATURE:
<221> NAME/KEY: CDS
<222> LOCATION: (1)..(39)
<223> OTHER INFORMATION: S100A1 cDNA [hinge-region]

<400> SEQUENCE: 33 ctc tct ggc ttc ctg gat gcc cag aag gat gtg gat gct              39
Leu Ser Gly Phe Leu Asp Ala Gln Lys Asp Val Asp Ala
 1               5                  10

<210> SEQ ID NO 34
<211> LENGTH: 13
<212> TYPE: PRT
<213> ORGANISM: Homo sapiens
<223> OTHER INFORMATION: S100A1 [hinge-region]

<400> SEQUENCE: 34

Leu Ser Gly Phe Leu Asp Ala Gln Lys Asp Val Asp Ala
 1               5                  10

<210> SEQ ID NO 35
<211> LENGTH: 33
<212> TYPE: DNA
<213> ORGANISM: Homo sapiens
<220> FEATURE:
<221> NAME/KEY: CDS
<222> LOCATION: (1)..(33)
<223> OTHER INFORMATION: S100A1 cDNA [C-terminal]

<400> SEQUENCE: 35 tat gtg gtg ctt gtg gct gct ctc aca gtg gcc                      33
Tyr Val Val Leu Val Ala Ala Leu Thr Val Ala
 1               5                  10

<210> SEQ ID NO 36
<211> LENGTH: 11
<212> TYPE: PRT
<213> ORGANISM: Homo sapiens
<223> OTHER INFORMATION: S100A1 [C-terminal]

<400> SEQUENCE: 36

Tyr Val Val Leu Val Ala Ala Leu Thr Val Ala
 1               5                  10
```

-continued

```
<210> SEQ ID NO 37
<211> LENGTH: 17
<212> TYPE: PRT
<213> ORGANISM: Homo sapiens
<223> OTHER INFORMATION: S100A1 [N-terminal, modified]

<400> SEQUENCE: 37

Gly Ser Glu Leu Glu Thr Ala Met Glu Thr Leu Ile Asn Val Phe His
 1               5                   10                  15

Ala

<210> SEQ ID NO 38
<211> LENGTH: 13
<212> TYPE: PRT
<213> ORGANISM: Homo sapiens
<223> OTHER INFORMATION: S100A1 [hinge-region, modified]

<400> SEQUENCE: 38

Leu Ser Gly Phe Leu Asp Ala Gln Lys Asp Ala Asp Ala
 1               5                   10

<210> SEQ ID NO 39
<211> LENGTH: 17
<212> TYPE: PRT
<213> ORGANISM: Homo sapiens
<223> OTHER INFORMATION: S100A1 [C-terminal, modified]

<400> SEQUENCE: 39

Asp Lys Asp Asp Pro Pro Tyr Val Val Leu Val Ala Ala Leu Thr Val
 1               5                   10                  15

Ala
```

TREATMENT OF CARDIAC POWER FAILURE

Figure 1A:
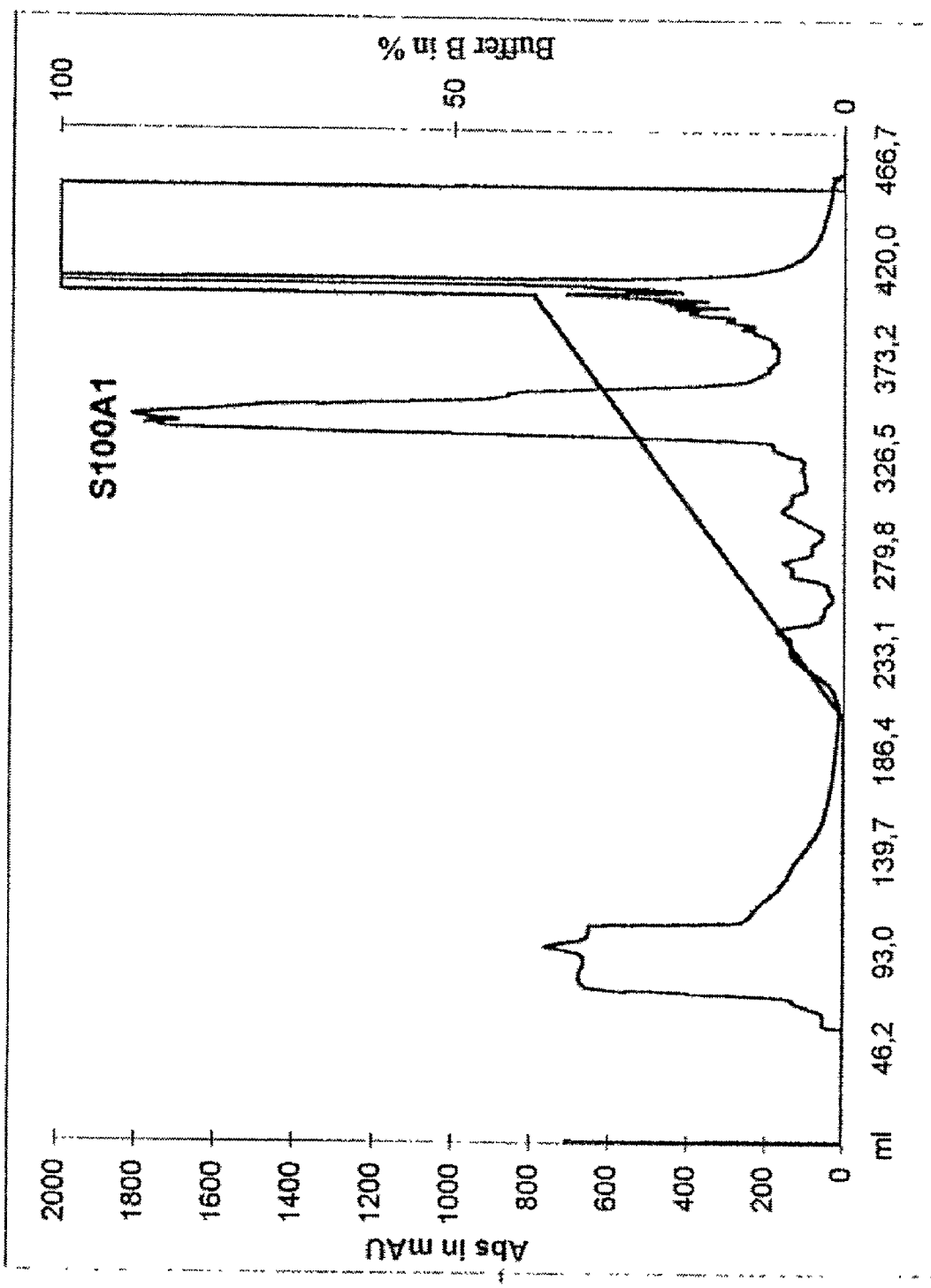

The present invention relates to medicaments for treating cardiac insufficiency which contain a therapeutically effective quantity of one or more S100 proteins, one or more mutants or fragments of same or nucleic acid sequence(s) coding for these amino acid sequences, optionally integrated into one or more gene transfer vectors.

Changes in intracellular $Ca^{2+}$ homeostasis play a pathophysiologically pivotal role in cardiac insufficiency at the molecular level. Gwathmey et al (1) were the first to detect prolonged intracellular $Ca^{2+}$ transients in contracting heart-muscle preparations of patients with end stage heart failure. Against the backdrop of an increased diastolic $Ca^{2+}$ level and reduced systolic $Ca^{2+}$ peaks (2), this finding was interpreted as an indication of a dysfunction of the sarcoplasmic reticulum (hereafter abbreviated to SR) which correlates at the haemodynamic level with an inverse force-frequency relationship of the myopathic heart muscle (3).

Of central importance here is the reduced re-uptake of $Ca^{2+}$ into the SR during the diastole through the $Ca^{2+}$ATPase ($Ca^{2+}$ pump of the SR which pumps the $Ca^{2+}$ out of the cytosol into the SR against a concentration gradient of 1:10,000). This leads on the one hand to a disturbed relaxation of the heart muscle during the diastole and to an associated reduction in $Ca^{2+}$ release during the systole and thus to a reduced force development of the heart muscle. Among others, this observation is based on the fact that insufficient hearts have reduced cAMP levels (4). The cAMP-dependent phosphorylation of phospholamban is a precondition for activation of the $Ca^{2+}$ ATPase of the SR.

One of the existing strategies for improving contractility therefore aimed at an increase in intracellular cAMP levels through the administration of phosphodiesterase inhibitors. Although this pharmacological approach leads to an improvement in cardiac performance in the short term, this therapy option was left for the chronic treatment of cardiac insufficiency, as it leads to a 53% excess mortality of the patients examined compared with placebo.

A further strategy pursued to date consists of using more effectively the reduced $Ca^{2+}$ supply during the systole through a sensitization of the contractile apparatus with $Ca^{2+}$ sensitizers that allow an increased strength development of the contractile apparatus for the same $Ca^{2+}$ concentration. Clinical studies carried out to date with pimobendan were disappointing however, as no significant improvement of the heart function compared with placebo was to be documented (7). There are still no clinical data for the inhomogenous group of new $Ca^{2+}$ sensitizers. However, with some $Ca^{2+}$ sensitizers, this therapeutic approach leads, through an increased $Ca^{2+}$ sensitivity of the contractile apparatus, to a deteriorated relaxation so that the therapeutic advantage of an increased systolic strength development is called into question by a disturbance of the diastole (8).

In the search for further molecular causes for a restricted function of the SR within the framework of cardiac insufficiency, a reduced $Ca^{2+}$ATPase activity in crude membrane preparations (crude membranes) of insufficient hearts was able to be measured for different animal models and also for humans, so that a changed protein composition of the SR was assumed to be the cause. However, studies of the gene expression of the SR proteins phospholamban, $Ca^{2+}$ATPase and ryanodine receptor yielded varying and partly contradictory data. Thus, various work groups (9, 10, 11) found a significant reduced expression of the genes coding for phospholamban and $Ca^{2+}$ATPase also at protein level, whilst Movsesian et al (12) and Schwinger et al (13) documented no significant expression differences and Arai et al (14) found a differential expression in the course of hypertrophy development. Although a significantly lower $Ca^{2+}$ATPase activity was detected in crude membrane preparations of terminally insufficient hearts (15), this finding was incomprehensible for highly purified membrane preparations of the sarcoplasmic reticulum (12). To date, the contradictory results have been attributed to varying analysis methods (12).

The object of the present invention is therefore to provide medicaments for the treatment of cardiac insufficiency, in particular for the treatment or improvement of the pumping capacity of the heart, restricted within the framework of cardiac insufficiency. The medicaments are preferably furthermore intended to increase heart power in general and to be suitable for a treatment of acute and chronic cardiac insufficiency.

This object is achieved in general according to the invention by using S100 proteins, the proteins either being used directly as active ingredient or an overexpression of S100 proteins in the heart muscle being effected through a gene-therapy approach.

S100 proteins belong like calmodulin to the group of $Ca^{2+}$-binding proteins with EF-hand $Ca^{2+}$-binding motifs of which over 200 are now known. The family of the S100 proteins itself comprises 19 members of which 13 are coded on a narrow gene cluster on chromosome 1q21. Functionally, these proteins are incorporated into the regulation of cell differentiation, cell cycle regulation, signal transduction as well as $Ca^{2+}$ homeostasis (16). In contrast to the ubiquitously expressed calmodulin, S100 proteins have a tissue-specific expression pattern (17). They therefore translate the $Ca^{2+}$ signal into a tissue-specific response by interacting with specific target proteins after binding of $Ca^{2+}$ to their EF hands (16). S100 proteins have a strongly preserved amino acid sequence with high homology within the S100 family. The amino acid and cDNA sequences are shown in the sequence protocol as SEQ ID NO: 1 to 30 (numerical code <210>).

By S100 proteins within the meaning of the invention are meant the complete native proteins, mutants of the S100 proteins, peptides (fragments) of the S100 proteins or peptide mutants (with a homology of at least 60%, preferably at least 90% and particularly preferably at least 95%) as well as recombinantly prepared proteins or peptides or mutants or synthetic peptides or mutants.

According to a particular version of the invention, the S100 protein is S100β (S100B), S100A1, S100A2, S100A4 or S100A6 (cf. Schäfer et al., Genomics 23 (1995) 638-643). In the following, by the term "S100 protein" or "protein" is alternatively also meant the named mutants or peptides. Because of the species-general homology of the S100 proteins according to the invention, proteins and sequences coding for them of any species (such as e.g. pig, cattle etc.) can be used, the corresponding human sequences being most preferred.

The subject of the present invention is therefore medicaments (pharmaceutical preparations) for the treatment of heart diseases with reduced contractility force of whatever cause (primary and secondary cardiomyopathies), which contain a therapeutically effective quantity of one or more S100 proteins (preferably S100β, S100A1, S100A2, S100A4 or S100A6), one or more mutants or fragments of same, which is optionally formulated with pharmaceutically compatible auxiliaries and/or supports.

According to a preferred version of the invention, the S100 protein S100A1, which contains the amino acid sequence shown in SEQ ID NO: 2, and the preferred fragments contain the amino acid sequences shown in SEQ ID NO: 32, 34 and 36. Predominantly hydrophobic peptides can be extended to improve the solubility at the C- or N-terminal with hydrophilic amino acids. Preferably, according to the invention, the truncated and/or modified fragments according to SEQ ID NO: 37, 38 and/or 39 can be used.

Either single proteins, mutants or peptides of those named serve as active ingredients, but any mixtures of same can also be used, such as e.g. a combination of at least two of the peptides shown in SEQ ID NO: 32, 34, 36, 37, 38 and 39.

Within the framework of the present invention, by primary cardiomyopathies are meant hereditary cardiomyopathies and cardiomyopathies due to spontaneous mutations, by secondary cardiomyopathies are meant ischaemic cardiomyopathy due to an arteriosclerosis, dilatative cardiomyopathy due to an infectious or toxic disease of the myocardium, hypertensive heart disease due to a pulmonary-arterial and/or an arterial hypertonia, structural heart diseases due to rhythm disturbances and diseases of the heart valves, the primary and secondary myopathies being the cause of the cardiac insufficiency. The present application therefore furthermore relates to medicaments for the treatment of cardiac insufficiency.

For application, a direct injection of purified S100 protein (or mutants or peptide) either intravenously, intraarterially or intracoronally and/or long-term also the oral administration of recombinant protein or synthetic peptide analogues is possible.

Within the framework of the present invention, it was surprisingly found that in the cell culture model, after treatment with S100 protein, in particular S100A1 protein, and after S100 gene addition (in particular S100A1), an increase in the shortening and relengthening speed of cultivated myocardial cells is to be documented, which correlates with changed intracellular $Ca^{2+}$ transients in the sense of an increased systolic $Ca^{2+}$ release from the SR and an accelerated $Ca^{2+}$ re-uptake into the SR (see examples). These results were also able to be confirmed with other proteins of the S100 family.

The invention therefore furthermore relates to medicaments for the treatment of primary and secondary cardiomyopathies as well as cardiac insufficiency, which contain nucleic acid sequence(s) coding for one or more S100 proteins or one or more mutants or fragments of same, the nucleic acid(s) optionally being formulated with pharmaceutically compatible auxiliaries and/or supports. These nucleic acid sequence(s) can also be contained in one or more gene transfer vectors. The nucleic acid sequences coding for the S100 proteins used according to the invention are reproduced in SEQ ID NO: 1 to 35, SEQ ID NO: 1 (S100A1 cDNA) being particularly preferred. According to a preferred version of the invention, a combination of at least two of the nucleic acid sequences coding for SEQ ID NO: 32, 24, 36, 37, 38 and 39 (in particular SEQ ID NO: 31, 33, 35 as well as sequences coding for SEQ ID NO: 37, 38 and 39) are used. In the gene-therapy approach, one or more gene transfer vectors comprising this combination are considered, i.e. the nucleic acid sequences named can either be cloned into several vectors (e.g. each singly), or the combination of the coding sequences can be contained in a single vector.

The nucleic acids or gene transfer vectors are optionally formulated for intravenous, intraarterial, intracoronal or oral application. A use of DNA in liposomal fractions represents a further possibility for application, even if it displays a lower transfection efficiency.

The subject of the present invention is thus furthermore the use of a construct which makes possible an overexpression of S100, preferably of S100A1, in the heart muscle. Preferred is a viral construct which contains the DNA of an S100 protein, in particular of the S100β, S100A1, S100A2, S100A4 and the S100A6 protein, and which is preferably applied coronarally via a coronary catheter, displaying the highest transfection efficiency after this application.

The present invention thus furthermore relates to a process for the preparation of a gene transfer vector coding for one or more S100 proteins or one or more mutants or fragments of same, in which nucleic acid sequence(s) coding for the protein(s), the mutant(s) or the fragment(s) is (are) cloned into one or more vectors suitable for gene therapy.

The coding nucleic acid sequence is preferably selected from the group of the nucleic acid sequences represented in SEQ ID NO: 1 to 30. According to a particularly preferred version of the invention, the S100 DNA (sequence coding for S100A1 according to SEQ ID NO: 1), or the nucleic acid sequences coding for the fragments according to SEQ ID NO 32, 34, 36, 37, 38 and/or 39 (in particular SEQ ID NO: 31, 33, 35 as well as sequences coding for SEQ ID NO: 37, 38 and 39) are used for the preparation of the gene transfer vectors or for direct application.

In principle, several viral vector systems are suitable for carrying out a transfection of the heart tissue with S100 DNA. Recent vector systems (G. Bilbao et al., FASEB J. 11 (1977) 624-634; A. Amalficano et al. J. Virol. 72 (1998) 926-933) can produce an improvement in gene-therapy efficiency due to the immunological side effects still being only minimal compared with known adenoviral vectors. Gene-therapy efficiency can be further optimized by using strong heart-specific promoters, such as e.g. through a α-myosin heavy-chain promoter.

The effect of the S100 proteins can furthermore be increased by using corresponding sense oligonucleotides but the use of anti-sense oligonucleotides for S100 inhibitory substances can also be considered. Sense oligonucleotides (or anti-sense oligonucleotides of antagonistically acting proteins/peptides) or S100 proteins can be transferred directly into the vascular wall of the coronary arteries. Using a balloon system with a gel surface as carrier substance for oligonucleotides or proteins, the transfer of these molecules into the endothelial layer of the vessel accompanied by inflation of the balloon is achieved. This application method is however restricted to the influencing of cardial contractility by improving the vascular function in the sense of an improvement of the endothelial or smooth-muscular function, as only a local increase in the S100 protein concentration can be achieved herewith.

The transfection with S100A1 DNA leads to an increased concentration of S100A1 protein in the heart tissue, an underexpression of S100A1 which occurs within the framework of the cardiac insufficiency thus being treated causally by gene therapy and the function of this protein guaranteed again. The positively inotropic and lusitropic effect of S100A1 in the heart tissue is to be emphasized. Under S100A1 gene therapy of cultivated myocardial cells, of reconstituted heart tissue (18), and in an in-vivo model of the rabbit heart, after overexpression of S100A1, there is a significantly increased velocity of concentration of at least 20% (positive inotropy) and an accelerated relaxation (positive lusitropy). This effect is based on an improved function of the sarcoplasmic reticulum, which is characterized by an accelerated as well as increased $Ca^{2+}$ release from the SR as well as re-uptake of $Ca^{2+}$ back into the SR. This is documented in some hitherto unpublished tests with bioluminescence-supported analysis of the intracellular $Ca^{2+}$ transients (see examples).

The advantage of this invention is in particular that the dysfunction of the SR which is pathognomonic for cardiac insufficiency is causally treated.

Within the framework of the present invention therefore, not only are medicaments for the treatment of (chronic) cardiac insufficiency made available, but also medicaments for the treatment of heart diseases which are understood to be the cause of a cardiac insufficiency, such as primary cardiomyopathies (e.g. hereditary cardiomyopathies, cardiomyopathies due to spontaneous mutations) and secondary cardiomyopathies (e.g. ischaemic cardiomyopathy due to an arteriosclerosis, dilatative cardiomyopathy due to an infectious or toxic disease of the myocardium, hypertensive heart disease due to a pulmonary-arterial and/or arterial hypertonia, structural heart diseases due to rhythm disturbances, disease of the heart valves, etc.).

A further advantage of this invention is that further functions are described for S100, in particular for S100A1 which can significantly broaden the gene-therapy approach to the treatment of cardiac insufficiency.

Studies by Donato and by Garbuglia et al (19, 20) showed an inhibition of the polymerization of microtubuli and of intermediate filaments by S100A1 in biochemical reconstitutive assays. Immunohistochemical analyses by Schaper et al (21) document a significant increase in the microtubule network and of random intermediate filaments in explanted hearts of patients with cardiac insufficiency of NYHA class IV (New York Heart Association IV) which leads to an increased viscous load of the insufficient myocardium and thus to a reduced contraction speed (22). The therapeutic overexpression of S100A1 can thus prevent a hyper cytoskeletal crosslinking and improve the contraction conditions by reducing the viscous load.

Data from Baudier et al (23) finally document an inhibition of protein kinase C through S100A1. As the activation of protein kinase C has a key position in the signal transduction cascade of the hypertrophy process leading to insufficiency (24), an inhibition of protein kinase C through increased S100A1 tissue levels in the insufficient myocardium could be of great therapeutic significance for a normalization of the signal transduction of the insufficient heart.

The following examples, figures and the sequence protocol are intended to explain the invention in more detail without limiting it to same.

EXAMPLE 1

Purification of Recombinant S100A1

Human recombinant S100A1 was prepared in genetically modified *E. coli*. For this purpose, the cDNA of S100A1 was cloned into a pGEMEX expression vector, competent *E. coli* were transformed with this vector and selected via an ampicillin resistance contained in the vector. The genetically modified bacteria were stored until their use in 50% glycerin at −80° C. and then mixed according to the following method: 3 ml LB medium with 100 µg/ml ampicillin were seeded from the storage vessel with an eyelet and incubated overnight at 37° C. The following day, the overnight culture was added to 250 ml LB medium with 100 µg/ml ampicillin and 30 µg/ml chloramphenicol.

The optical density was measured every 30 minutes, and with OD>0.5 120 µl 1 M IPTG were added. After a further 3-4 hours, the medium was centrifuged off and the pellets were frozen and thawed 3-4 times to lyse the bacteria.

Figure 1B:
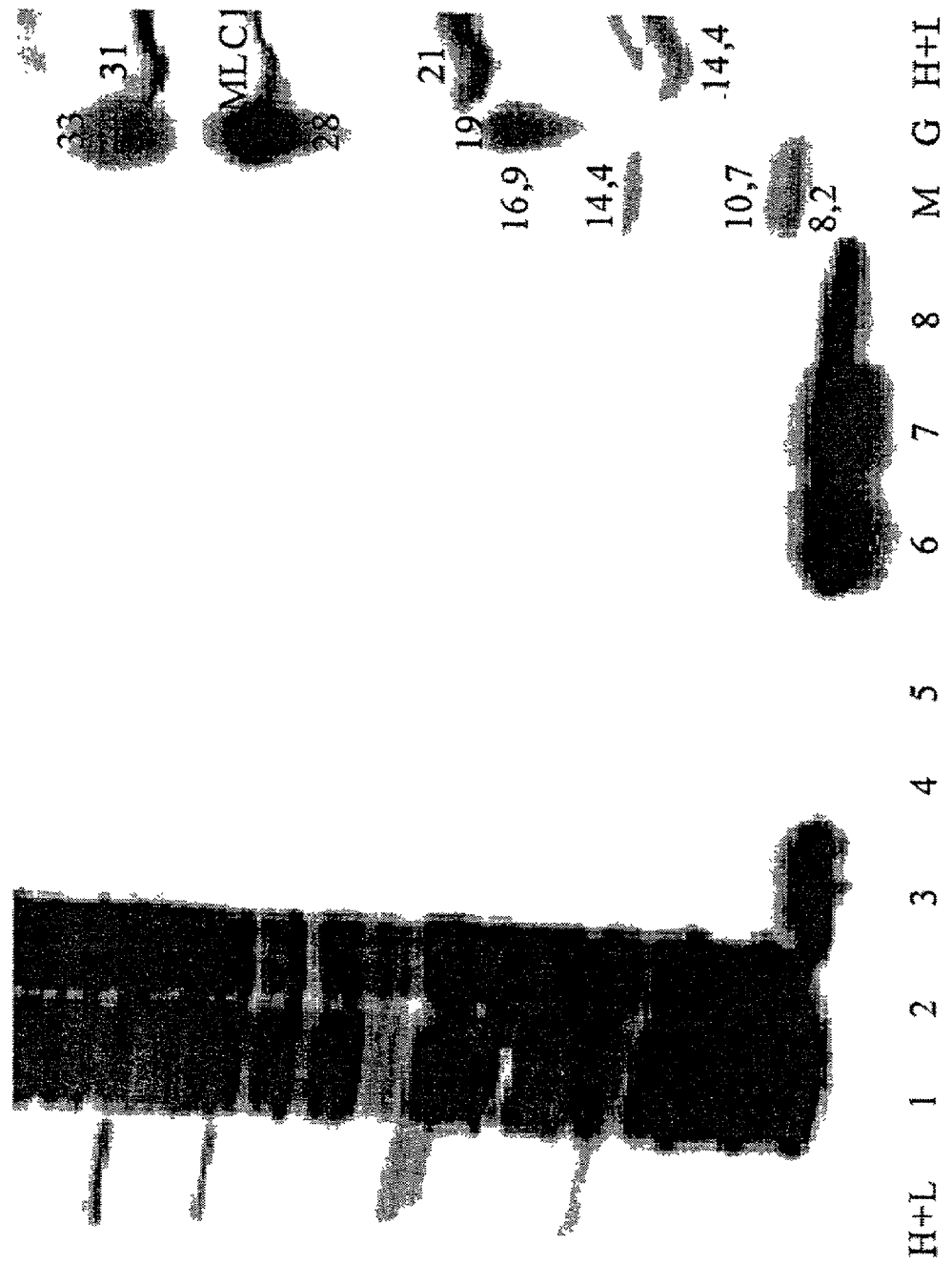

The bacterial pellets were homogenized in extraction buffer (25 mM tris-HCl, pH 7.5, 50 mM KCl, 1 mM PMSF, 5 mM EDTA) by means of ultrasound. The supernatants were brought to an end concentration of 2 M with saturated ammonium sulphate solution, and centrifuged off. The supernatant of ammonium sulphate precipitation was applied to a HiTrap octyl-sepharose column (Phamacia, Freiburg), which was equilibrated in advance with buffer A (25 mM tris-HCl, pH 7.5, 2 mM CaCl2). The S100A1 bound to the column was eluted with a stepped gradient to buffer B (25 mM tris-HCl, pH 9.5, 5 mM EGTA). To achieve a purity of more than 95%, the S100 eluate was then subjected to an anion exchange chromatography. The sample was deposited on a HiTrapQ column (Pharmacia) previously equilibrated in buffer A (25 mM tris-HCl, pH 7.5) and eluted through a linear gradient to 40% buffer B (25 mM tris-HCl, pH 7.5, 1 M NaCl). The purified S100A1 was concentrated in a vacuum evaporator and dialyzed against 10 mM HEPES (pH 7.5) and then stored in aliquots at −80° C. FIG. 1*a* shows the elution profile of the HiTrapQ column and an SDS polyacrylamide gel and FIG. 1B the associated Western Blot which is carried out for quality control of the S100A1 purification. It is seen that the purification procedure used leads to a high degree of purity of the S100A1 protein.

EXAMPLE 2

Increased Intracellular $Ca^{2+}$ Transients in Cultivated Neonatal Rat Cardiomyocytes After Co-Cultivation with Recombinant S100A1

Neonatal rat hearts were removed from 3-day-old rats, ventricles separated from the atria and stored coarse-ground on ice in ADS buffer (6.8 g NaCl, 4.76 g HEPES, 0.12 g $NaH_2PO_4$, 1 g glucose, 0.4 g KCl, 0.1 g $MgSO_4$ and 1000 ml $H_2O$). In a bioreactor (Wheaton® container), the cells were then separated from the tissue assembly by means of collagenase digestion (108 U/mg/ml collagenase, Worthington, USA), and the released cells separated over a density gradient (Percoll, Pharmacia®) by centrifugation. The cardiomyocyte fraction was resuspended in cell culture medium (DMEM+ 10% newborn calf serum) and plated in a density of approx. 100,000 cardiomyocytes per well on 24-well cell culture plates. After 24 hours culture at 37° C. and 5% $CO_2$, recombinant S100A1 was added to the cell culture medium at two-day intervals in concentrations of 1 µM to 10 µM. After 7 days, the measurement of the calcium transients after 1 hour's loading of the cells with FuraPE3AM® took place. The intracellular $Ca^{2+}$ transients were then detected and quantified by means of inverse fluorescence microscopy (Olympus OSP 3®) under both rest conditions and electrical field stimulation (PHYWE®-bioelectrical measurement unit; frequencies of 30-300 bpm). FIG. 2 shows the original derivations of the analyzed control cells (2*a*) and of the cells treated with S100A1 (2*b*). The statistical evaluation shows that under stimulation with S100A1, the rise in the $Ca^{2+}$ concentration per time unit in the systole (+dc/dt) is significantly increased by 3 times (p<0.0002) in comparison with the control cell population. The drop in the $Ca^{2+}$ concentration per time unit in the diastole (−dc/dt) is accelerated by 2.2 times (p<0.0003) under S100A1 stimulation in comparison with the control cell population. The changes in the $Ca^{2+}$ concentration per time unit were measured as a quotient from the time until the signal maximum and the signal amplitude (+dc/dt) were reached or as a quotient of the time until the half amplitude and the signal amplitude (−dc/dt) were reached. It can be shown with this test approach that S100A1 as a paracrine factor improves the efficiency of the SR function.

EXAMPLE 3

Preparation of the S100A1 Overexpressing Virus Construct

To prepare the S100A1 overexpressing virus construct, the following strategy is applied: The S100A1 DNA is cloned into the multi cloning site behind a CMV promoter into the adenoviral shuttle-vector pAD TRACK (Tong-Chuan He et al. Proc Natl Acad Sci 95; 2509-2514). The resulting plasmid is linearized with PME1 and recombined with pEASY (Tong-Chuan He et al. Proc Natl Acad Sci 95; 2509-2514) in *E. coli* BJ 5183. The recombination product (pAD/S100A1) corresponds to a plasmid which contains the viral DNA of the E1 and E3 deleted adenovirus type 5, the S100A1 DNA and a kanamycin resistance. Samples of the plasmid pAD/S100A1 were deposited on 26 Mar. 1999 at the DSMZ-Deutsche Sammlung von Mikroorganismen und Zellkulturen GmbH [German Collection of Microorganisms and Cell Cultures], Mascheroder Weg 1b, 38124 Brunswick, under the accession number DSM 12755 under the Budapest Treaty. pAD/S100A1 is then transformed in *E. coli* DH5$_\alpha$ accompanied by kanamycin selection (50 µg/ml) and multiplied. pAD/S100A1 is linearized with PAC1 accompanied by loss of the kanamycin resistance and incorporated by means of lipofectamin (Gibco, BRL) into HEK293 cells for virus production. After 10 days, the virus is harvested with a low titre and HEK293 infected again. After several cycles of harvesting and reinfecting of HEK293 cells, a high-titre virus finally results which is processed as follows before being introduced into the organism: The HEK293 cells are harvested prior to the cell lysis and centrifuged off (3400 rpm×10 min). The resulting HEK cell pellet is washed twice in PBS (0.01 M, Sigma, p-3813) and finally taken up in 0.01 M TRIS-pH 8.1. The virus-containing HEK293 cells are then lysed by being frozen four times (liquid nitrogen) and thawed (at 37° C.), and the virus released. HEK cell DNA is removed by DNAse digestion (at 37° C. over 30 minutes) and HEK cell proteins by freon extraction from the lysate. The virus is purified by means of ultracentrifugation (12 h×127000 g) through a caesium chloride gradient. The resulting virus fraction is removed and dialyzed for 3×2 hours (1 vol-% saccharose in 0.01 M PBS pH 7.4) and stored in aliquots at −80° C. For a gene-therapy treatment, between $10^9$ to $10^{12}$ virus particles are used per gram of heart tissue.

EXAMPLE 4

Gene Therapy of the Rabbit Heart: Increasing the +dP/dt and the Systolic Ejection Pressure as a Result of Viral Overexpression of the Ca$^{2+}$-Binding Protein S100A1 in the Rabbit Myocardium In the 4$^{th}$ ICR, the thorax of New Zealand white rabbits was opened on the right side by lateral thoracotomy. After the aorta was displayed, the opening of the pericardium and the ligation of the aorta took place. By left-cavity injection, an intracoronal perfusion with 2×10$^{11}$ virus particles of the recombinant S100A1 virus (n=6), of a virus without S100A1 cDNA (n=11) or of NaCl (n=11) was achieved. 7 days after the operation, the rabbit was catheterized via the a. carotis. The contraction speed (dP/dt) and the systolic ejection pressure (SEP) of the rabbit hearts were measured under basal conditions as well as under isoprenerol stimulation (0.1, 0.5 and 1.0 µg/kg/min). Cryosections were prepared from the rabbit myocardium deep-frozen in liquid nitrogen, and the virus infection of the myocardium demonstrated by fluorescence microscope measurement of the GFP expression (see FIG. 3).

The injection of a virus construct without S100A1 cDNA results in a reduction in the systolic ejection pressure (SEP in mmHg) of the rabbit hearts of 9% on average under all raised conditions in comparison with the animals treated with NaCl. Under basal conditions, the behaviour of the SEP in the case of the animals treated with S100A1 is statistically not significantly different from both control groups. The SEP in the S100A1 group of the overexpressing rabbits increases by 17% (0.1 µg/kg/min; p<0.02), 10% (0.5 µg/kg/min; p=0.06) and 11% (1.0 µg/kg/min; p<0.05) compared with the group which was treated with the virus construct without S100A1 cDNA under all isoprenerol stimulations. Under isoprenerol stimulation, the animals treated with S100A1 have a SEP which is 4% higher (n.s) compared with the NaCl group (see FIG. 4a).

The contraction speed (dP/dt in mm Hg/s) of the heart falls by an average of 10% upon application of a virus construct without S100A1 cDNA compared with the NaCl injection under all measured conditions which we attribute to a myocarditis. The S100A1 overexpressing animals showed no statistically deviating dP/dt under basal conditions compared with the virus control group. By contrast, the contractility of the heart increased in the S100A1 group under isoprenerol stimulation by 17% (0.1 µg/kg/min; p<0.05), 14% (0.5 µg/kg/min; p<0.03) and 14% (1.0 µg/kg/min; p<0.05) compared with the virus control. The animals treated with the recombinant S100A1 virus showed a dP/dt increased on average by 5% (n.s.) compared with the NaCl group, despite the myocarditis (see FIG. 4b).

EXAMPLE 5

Increasing the Force Transients of Skinned Fibres Preparations of the Skeletal Muscle of the Rat Through Recombinant S100A1 and Through Peptides of this Protein The binding of Ca$^{2+}$ to S100A1 leads to a modified tertiary structure of this Ca$^{2+}$-binding protein, resulting in a narrow spatial coordination of the three hydrophobic protein portions (1 amino acids 2-16 [N terminal], cf. SEQ ID NO: 32; 2 amino acids 42-54 [hinge region], cf. SEQ ID NO: 34; 3 amino acids 75-85 [C terminal], cf. SEQ ID NO: 36), which together bind to the RyR (ryanodine receptor is a synonym for Ca$^{2+}$ATPase of the SR), as data from Treves et al (25) suggest. The aim of this test procedure was therefore to examine what functional significance these sequences—in the form of synthetic peptides—have compared with the whole protein for the regulation of the Ca$^{2+}$ release from the SR. The Ca$^{2+}$ release was measured indirectly on saponin-semipermeabilized skeletal muscle fibres of the rat over an isometric force gradient. The measurement of the isometric force before and after addition of S100A1 peptide/protein served as a control.

Whereas the individual peptides showed no effect, the combination of "C-terminal" peptide and the "hinge region" increased the isometric force development already by 15%±4%. Both the combination of the three peptides (FIG. 5b) and the recombinant protein (FIG. 5a) in equimolar concentration (5-10 µM) increased the maximum force development in slow skeletal musculature (M. soleus) in the same way by 49%±6% and 52%±7% respectively compared with the control with an unchanged $Ca^{2+}$ sensitivity of the contractile apparatus.

These results show that the effects of S100A1 can be simulated by the hydrophobic protein portions and the full effect of the native protein triggered only by the combination of all three peptides. They thus show the significance of the $Ca^{2+}$-dependent coordinative regulation of the RyR through the hydrophobic sequences of S100A1.

LEGENDS OF THE FIGURES

FIG. 1: (a) Elution profile of HiTrapQ, absorption at 220 nm.
  (b) Silver stain after SDS polyacrylamide gel electrophoresis of the individual purification stages: 1: extract from E. coli, 2: proteins not bound by octyl-sepharose, 3: EGTA eluate of octyl sepharose, 4-5: proteins not bound by HiTrapQ, 6-8: fractions of the S100A1 peak of HiTrapQ.

Figure 2A:
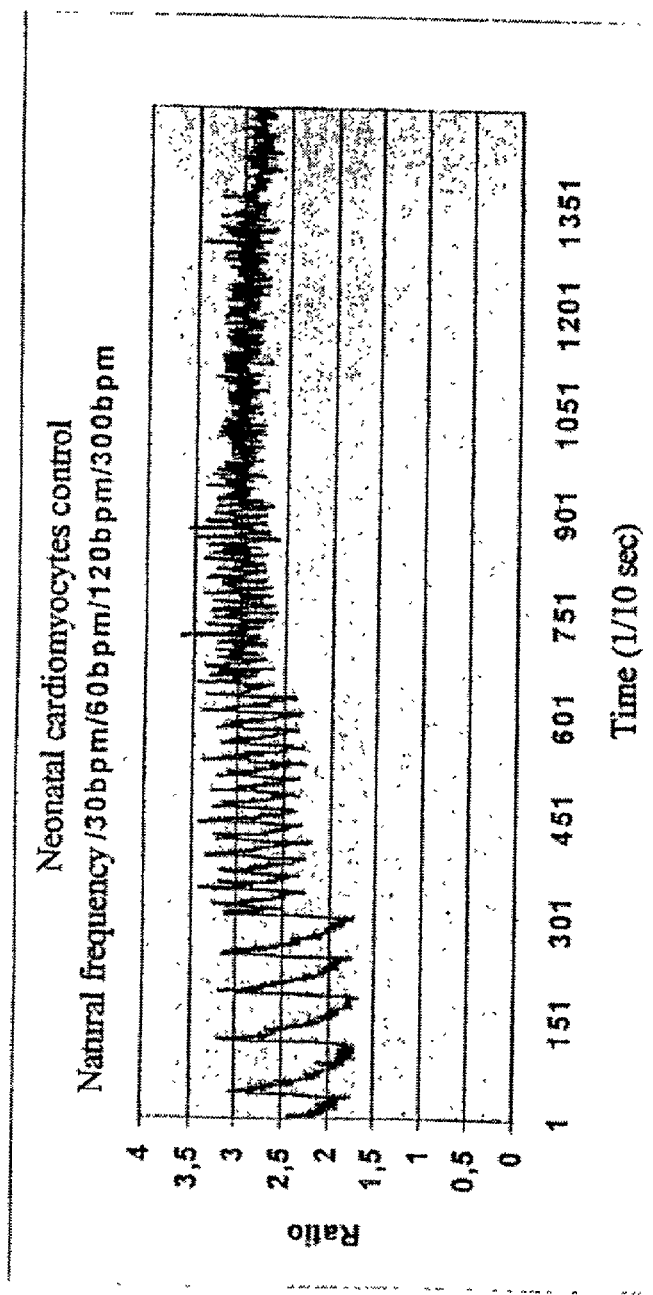
Figure 2B:
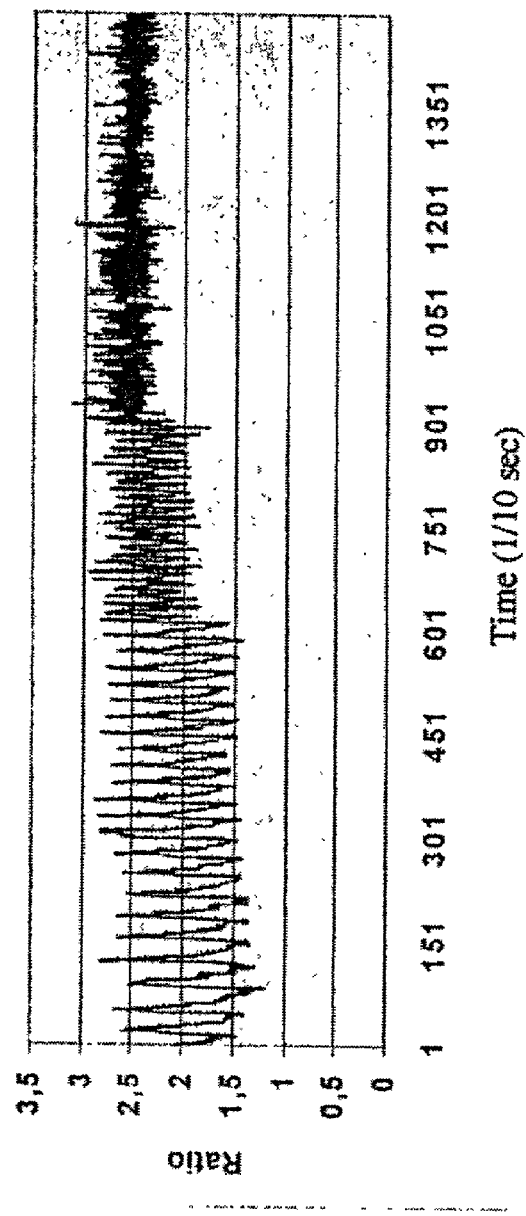

FIG. 2: original tracings of the analyzed control cells (FIG. 2a) and of the cells treated with S100A1 (FIG. 2b).

Figure 3:
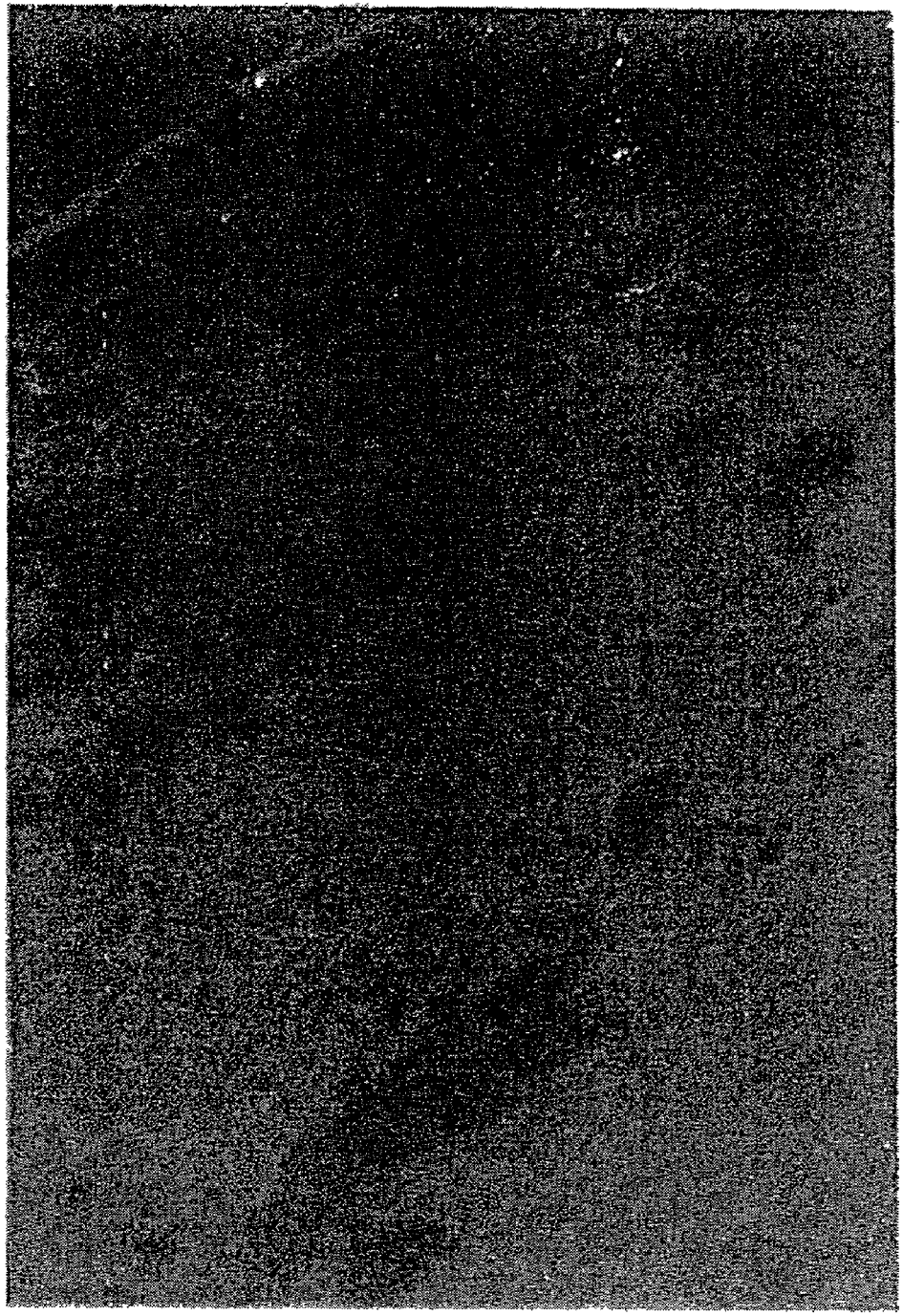

FIG. 3: Detection of the viral infection of the myocardium by fluorescence microscope measurement of the GFP expression in cryosections of deep-frozen rabbit myocardium.

Figure 4A:
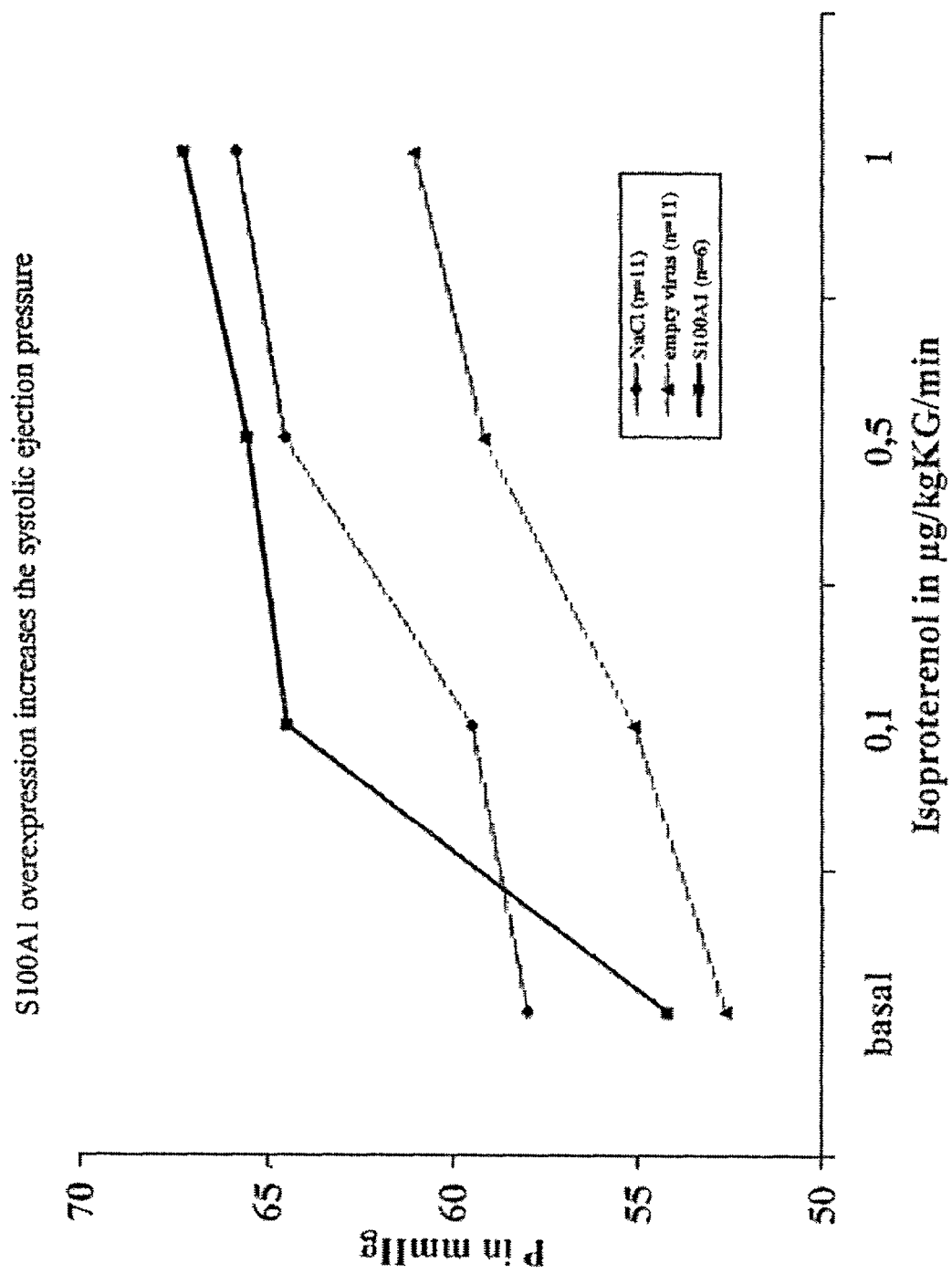
Figure 4B:
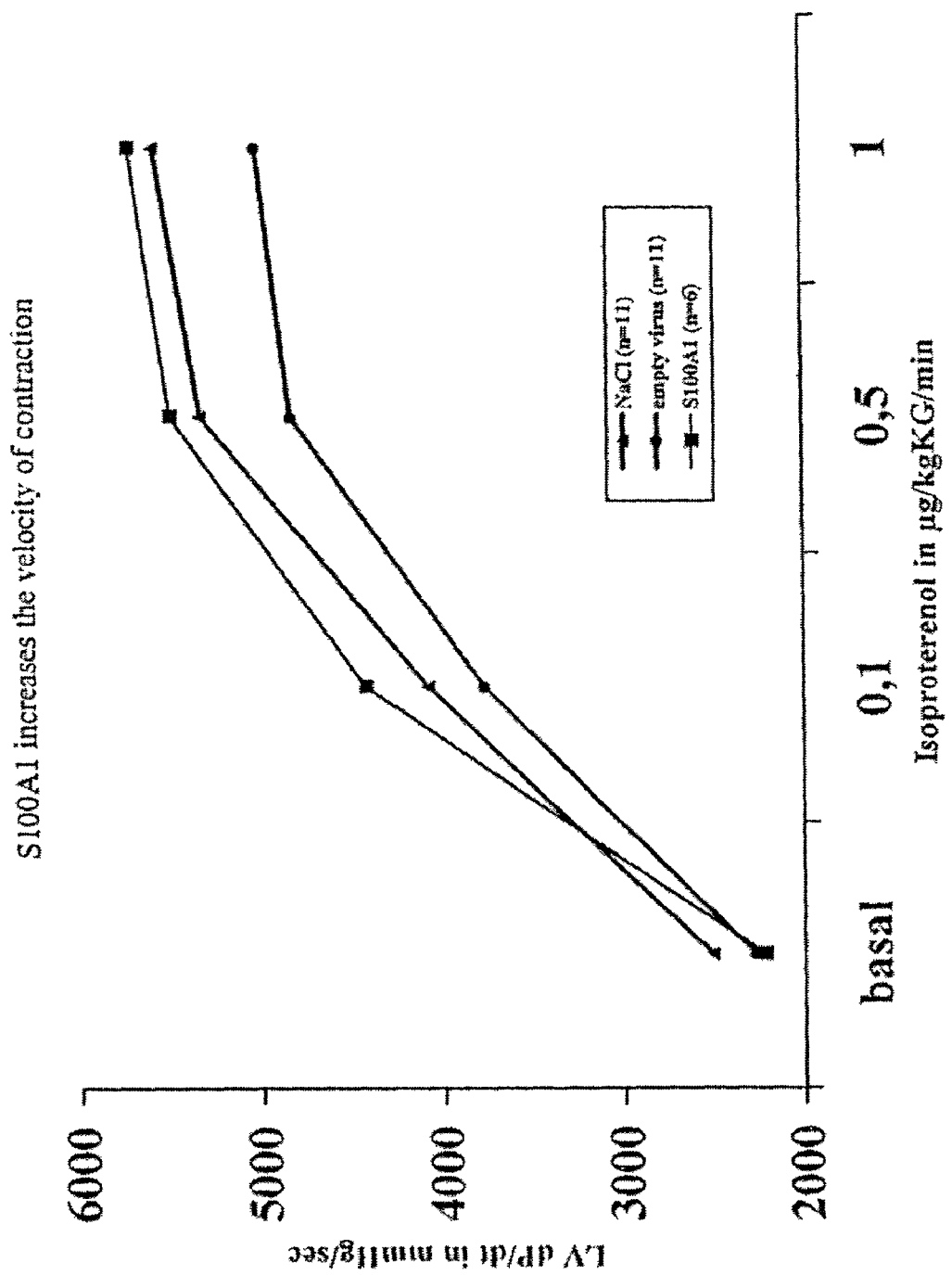

FIG. 4: Systolic ejection pressure under isoproterenol stimulation in animals treated with S100A1 compared with the control group (FIG. 4a). Contraction speed under isoproterenol stimulation in animals treated with S100A1 compared with the control group (FIG. 4b).

Figure 5A:
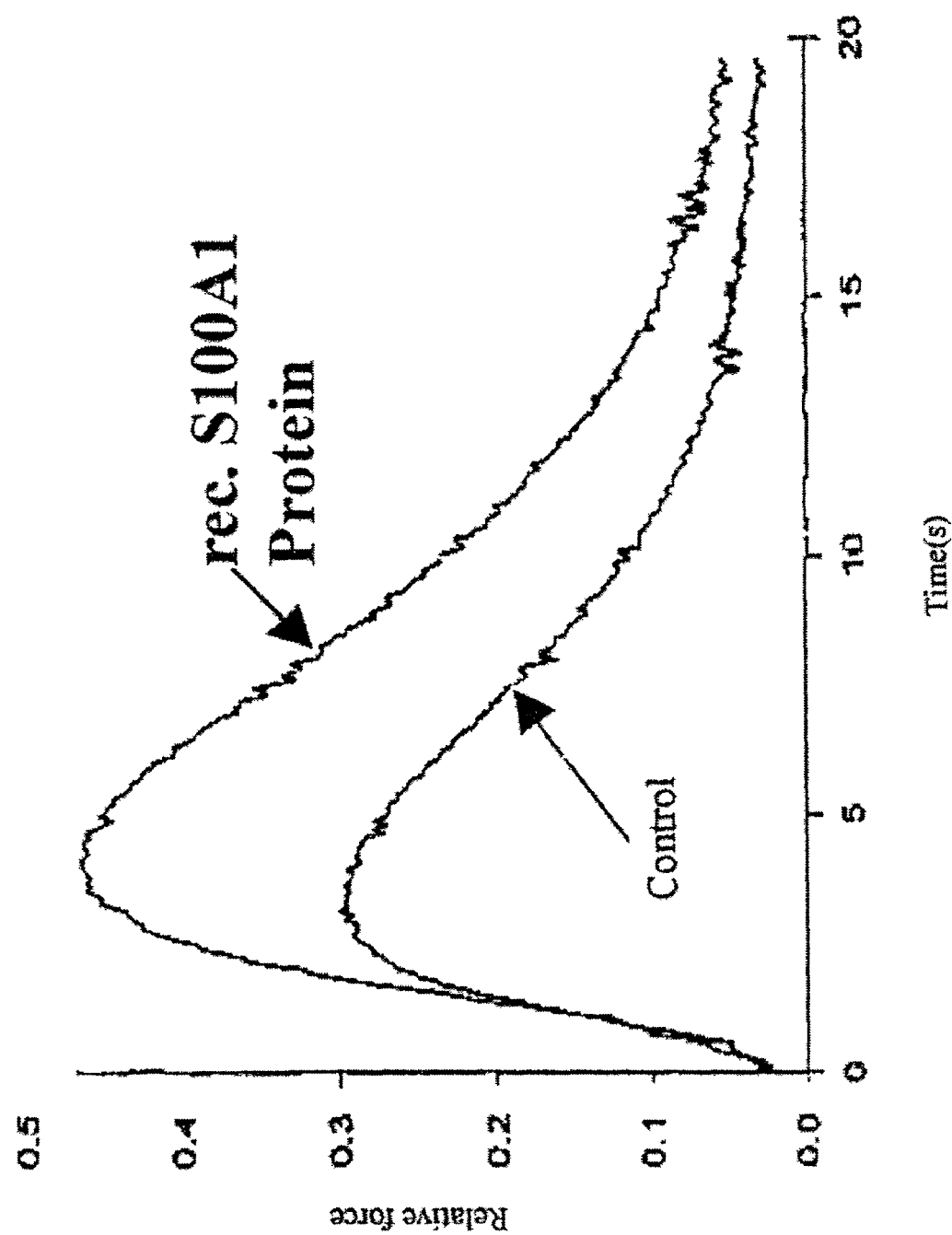
Figure 5B:
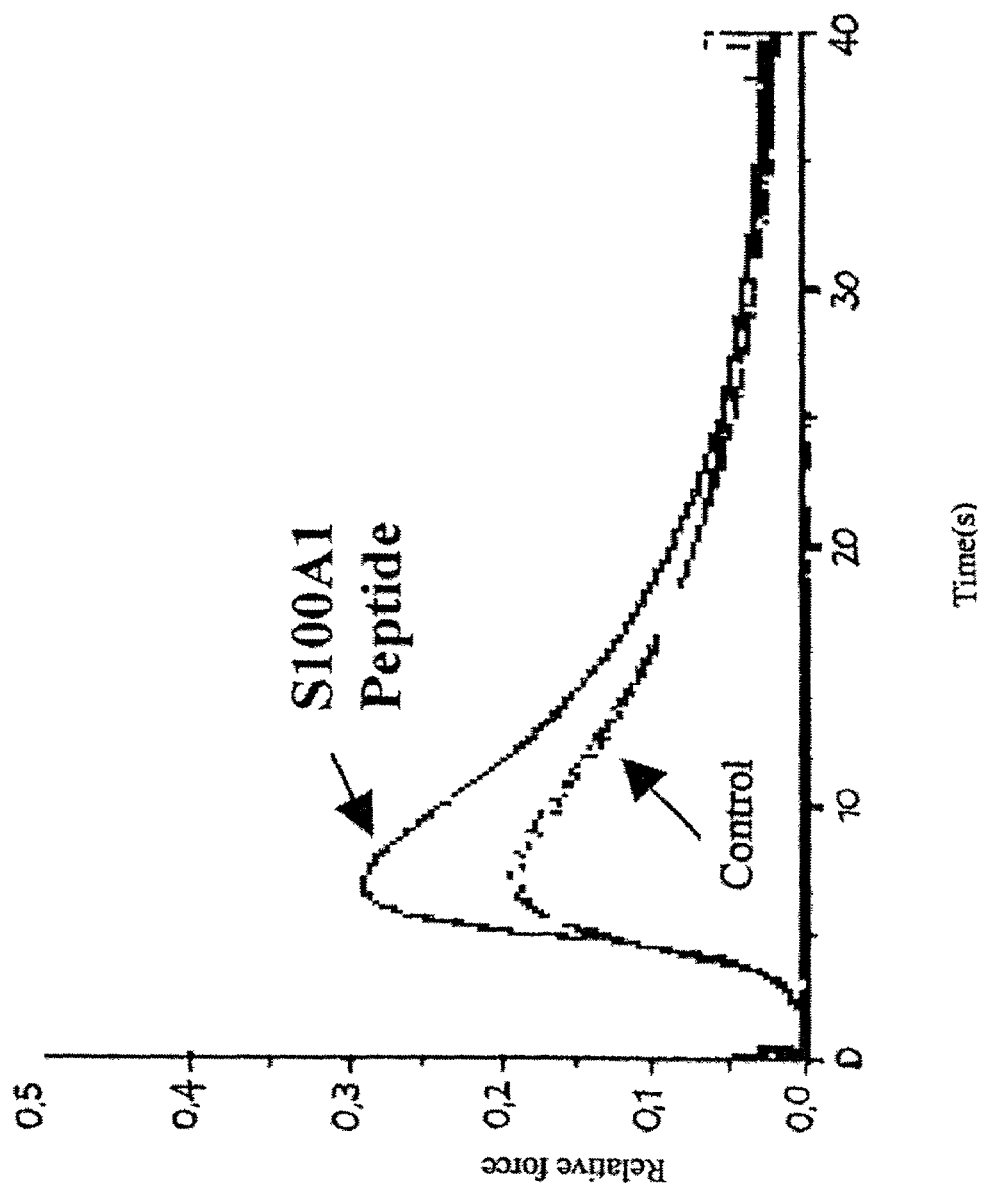

FIG. 5: Increasing the maximum force development in slow skeleton musculature (M. soleus) by combining the three S100A1 peptides (N-terminal, hinge region, C-terminal; FIG. 5b) and by recombinant S100A1 protein (FIG. 5a) in equimolar concentration (5-10 µM).

REFERENCES (1) Gwathmey J K, Copelas L, MacKinnon R, Schoen F J, Feldman M D, Grossman W, Morgan J P. Abnormal intracellular calcium handling in myocardium from patients with end-stage heart failure. Circ Res 1987 July; 61 (1): 70-76

(2) Beuckelmann D J, Nabauer M, Erdmann E. Intracellular calcium handling in isolated ventricular myocytes from patients with terminal heart failure. Circulation 1992 March; 85 (3): 1046-1055

(3) Hasenfuss G, Holubarsch C, Hermann H P, Astheimer K, Pieske B, Just H. Influence of the force-frequency relationship on haemodynamics and left ventricular function in patients with non-failing hearts and in patients with dilated cardiomyopathy. Eur Heart J 1994 February; 15 (2): 164-170

(4) Bohm, Reiger B, Schwinger R H, Erdmann E cAMP concentrations, cAMP dependent protein kinase activity, and phospholamban in non-failing and failing myocardium. Cardiovasc Res 1994 November; 28 (11): 1713-9

(5) Packer M, Carver J R, Rodeheffer R J, Ivanhoe R J, DiBianco R, Zeldis S M, Hendrix G H, Bommer W J, Elkayam U, Kukin M L, et al Effect or oral milrinone on mortality in severe chronic heart failure. The PROMISE Study Research Group. N Engl J Med 1991 Nov. 21; 325 (21): 1468-75

(6) Cruickshank J M Phosphodiesterase III inhibitors: long-term risks and short-term benefits. Cardiovasc Drugs Ther 1993 August; 7 (4): 655-60

(7) Reddy S, Benatar D, Gheorghiade M Update on digoxin and other oral positive inotropic agents for chronic heart failure. Curr Opin Cardiol 1997 May; 12 (3): 233-41

(8) Zimmermann N, Boknik P, Gams E, Herzig J W, Neumann J, Scholz H Calcium sensitization as new principle of inotropic therapy in end-stage heart failure? Eur J Cardiothorac Surg 1998 July; 14 (1): 70-5

(9) Hasenfuss G, Reinecke H, Studer R, Meyer M, Pieske B, Holtz J, Holubarsch C, Posival H, Just H, Drexler H Relation between myocardial function and expression of sarcoplasmic reticulum Ca(2+)-ATPase in failing and nonfailing human myocardium. Circ Res 1994 September; 75 (3): 434-442

(10) Meyer M, Schillinger W, Pieske B, Holubarsch C, Heilmann C, Posival H, Kuwajima G, Mikoshiba K, Just H, Hasenfuss G, et al Alterations of sarcoplasmic reticulum proteins in failing human dilated cardiomyopathy Circulation 1995 August 15; 92 (4): 778-784.

(11) Studer R, Reinecke H, Bilger J, Eschenhagen T, Bohm M, Hasenfuss G, Just H, Holtz J. Drexler H. Gene expression of the cardiac Na(+)-Ca2+ exchanger in end-stage human heart failure. Circ Res 1994 September; 75 (3): 443-453

(12) Movsesian M A, Karimi M, Green K, Jones L R Ca)2+)-transporting ATPase, phospholamban, and calsequestrin levels in nonfailing and failing human myocardium. Circulation 1994 August; 90 (2): 653-657

(13) Schwinger R H, BOHM M, Schmidt U, Karczewski P, Bavendiek U, Flesch M, Krause E G, Erdmann E. Unchanged protein levels of SERCA II and phospholamban but reduced Ca2+ uptake and Ca(2+)-STPase activity of cardiac sarcoplasmic reticulum from dilated cardiomyopathy patients compared with patients with nonfailing hearts. Circulation 1995 December 1; 92 (11): 3220-3228

(14) Arai M, Suzuki T, Nagai R. Sarcoplasmic reticulum genes are upregulated in mild cardiac hypertrophy but downregulated in severe cardiac hypertrophy induced by pressure overload. J Mol Cell Cardiol 1996 August; 28 (8): 1583-1590

(15) Schmidt U, Hajjar R J, Helm P A, Kim C S, Doye A A, Gwathmey J K Contribution of abnormal sarcoplasmic reticulum ATPase activity to systolic and diastolic dysfunction in human heart failure. J Mol Cell Cardiol 1998 October; 30 (10): 1929-37

(16) Schäfer B W, Heizmann C W The S100 family of EF-hand calcium-binding proteins: functions and pathology. Trends Biochem Sci 1996 April; 21 (4):

(17) Kato K, Kimura S. S100ao (alpha alpha) protein is mainly located in the heart and striated muscles. Biochim Biophys Acta 1985 Oct. 17; 842 (2-3): 146-150

(18) Eschenhagen T et al, FASEB J. 11, 683-694; 1997

(19) Donato R. Effect of S-100 protein on assembly of brain microtubule proteins in vitro. FEBS Lett 1983 Oct. 17; 162 (2): 310-313

(20) Garbuglia M, Verzini M, Giambanco I, Spreca A, Donato R. Effects of calcium-binding proteins (S-100a(o), S-100a, S-100b) on desmin assembly in vitro. FASEB J 1996 February; 10 (2): 317-324

(21) Schaper J, Froede R, Hein S, Buck A, Hashizume H, Speiser B, Friedl A, Bleese N. Impairment of the myocardial ultrastructure and changes of the cytoskeleton in dilated cardiomyopathy. Circulation 1991 February; 83 (2): 504-514

(22) Tsutsui H, Ishihara K, Cooper G 4$^{th}$ Cytoskeletal role in the contractile dysfunction of hypertrophied myocardium. Science 1993 Apr. 30; 260 (S108): 682-687

(23) Baudier J, Bergeret E, Bertacchi N, Weintraub H, Gagnon J, Garin J Interactions of myogenic bHLH transcription factors with calcium-binding calmodulin and S100a (alpha alpha) proteins. Biochemistry 1995 Jun. 20; 34 (24): 7834-7846
(24) Wakasaki H, Koya D, Schoen F J, Jirousek M R, Ways D K, Hoit B D, Walsh R A, King G L Targeted overexpression of protein kinase C beta2 isoform in myocardium causes cardiomyopathy. Proc Natl Acad Sci USA 1997 Aug. 19; 94 (17): 9320-5
(25) Treves S, Scutari E, Robert M, Groh S, Ottolia M, Presipino G, Ronjat M, Zorzato F Interaction of S100A1 with the Ca2+ release channel (ryanodine receptor) of skeletal muscle. Biochemistry 1997 Sep. 23; 36 (38): 11496-11503

The invention claimed is:

1. A method for treating cardiac insufficiency in a subject, comprising administering to the subject a compatible auxiliary or support and a nucleic acid encoding a polypeptide selected from the group consisting of at least one S100A1 protein, wherein S100A1 contains the amino acid sequence shown in SEQ ID NO:2 or has at least 95% homology thereto, and a plurality of hydrophobic fragments of said S100A1 selected from the group consisting of the amino acid sequences shown in SEQ ID NO:34 and SEQ ID NO:36 or having at least 90% homology thereto, wherein said polypeptide increases the systolic $Ca^{2+}$ release from the sarcoplasmic reticulum and increases the rate of $Ca^{2+}$ uptake into the sarcoplasmic reticulum, wherein said nucleic acid is administered intracoronally.

2. The method of claim 1, wherein the nucleic acid is contained within a gene transfer vector.

3. The method of claim 1, wherein S100A1 contains the amino acid sequence shown in SEQ ID NO: 2.

4. The method of claim 1, wherein the fragments are selected from the group consisting of the amino acid sequences shown in SEQ ID NO:34 and SEQ ID NO:36.

5. The method of claim 1, wherein the fragments are a combination of the two amino acid sequences according to SEQ ID NO:34 and SEQ ID NO:36.

6. The method of claim 1, wherein the nucleic acid sequence comprises the sequence shown in SEQ ID NO:1.

7. The method of claim 1, wherein the nucleic acid comprises a sequence selected from the group consisting of SEQ ID NO:33 and SEQ ID NO:35.

8. The method of claim 1, wherein the nucleic acid comprises the two nucleic acid fragments according to SEQ ID NO:33 and SEQ ID NO:35.

9. A method for increasing heart contractility or systolic ejection pressure in a subject, comprising intracoronally administering to the subject a nucleic acid encoding an S100A1 protein, wherein S100A1 contains the amino acid sequence shown in SEQ ID NO:2 or has at least 95% homology thereto, whereby said administration increases heart contractility or systolic ejection pressure.

10. The method of claim 9, wherein the nucleic acid is contained within a gene transfer vector.

11. The method of claim 10, wherein the gene transfer vector is an adenoviral vector.

12. The method of claim 9, wherein S100A1 contains the amino acid sequence shown in SEQ ID NO:2.

13. A method for increasing heart contractility or systolic ejection pressure in a subject, comprising intracoronally administering to the subject a nucleic acid encoding a peptide having an amino acid sequence selected from the group consisting of SEQ ID NO:34 and SEQ ID NO:36 or having at least 90% homology thereto, whereby said administration increases heart contractility or systolic ejection pressure.

14. The method of claim 13, comprising administering two nucleic acids encoding a peptide having an amino acid sequence selected from the group consisting of SEQ ID NO:34 and SEQ ID NO:36.

15. The method of claim 9, wherein the nucleic acid sequence comprises the sequence shown in SEQ ID NO:1.

16. The method of claim 13, wherein the nucleic acid has the sequence of SEQ ID NO:33 or SEQ ID NO:35.

17. The method of claim 14, wherein the nucleic acid comprises two nucleic acid fragments selected from the group consisting of SEQ ID NO:33 and SEQ ID NO:35.

18. A method for treating cardiac insufficiency in a subject, comprising directly delivering a composition comprising a nucleic acid encoding an S100A1 protein, wherein S100A1 contains the amino acid sequence shown in SEQ ID NO:2 or a fragment comprising SEQ ID NO: 34 or SEQ ID NO: 36 and a compatible auxiliary or support to the heart of a subject in need of such treatment.

19. The method according to claim 1, wherein the nucleic acid encodes a polypeptide selected from the group consisting of at least one S100A1 protein, wherein S100A1 contains the amino acid sequence shown in SEQ ID NO:2, and a plurality of hydrophobic fragments of said S100A1 having at least 95% homology to amino acids sequences selected from the group consisting of SEQ ID NO:34 and SEQ ID NO:36.

20. The method according to claim 1, wherein the nucleic acid encodes a polypeptide selected from the group consisting of at least one S100A1 protein, wherein S100A1 contains the amino acid sequence shown in SEQ ID NO:2, and a plurality of hydrophobic fragments of said S100A1 selected from the group consisting of the amino acid sequences shown in SEQ ID NO:34 and SEQ ID NO:36.

\* \* \* \* \*